US007902401B2

(12) United States Patent
Higgins et al.

(10) Patent No.: US 7,902,401 B2
(45) Date of Patent: Mar. 8, 2011

(54) FLUORINATED COMPOUNDS

(75) Inventors: Guy A. Higgins, Toronto (CA); Methvin Issac, Toronto (CA); Abdelmalik Slassi, Toronto (CA); Tao Xin, Toronto (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 419 days.

(21) Appl. No.: 11/610,864

(22) Filed: Dec. 14, 2006

(65) Prior Publication Data
US 2009/0005433 A1 Jan. 1, 2009

(51) Int. Cl.
C07C 233/05 (2006.01)
A61K 31/16 (2006.01)
(52) U.S. Cl. ............ 564/194; 564/155; 560/29; 560/30; 560/31; 549/75; 549/76; 514/438; 514/478; 514/616; 514/620
(58) Field of Classification Search .................. 514/438, 514/485, 605, 616, 478, 620; 564/194, 155; 560/29, 30, 31; 549/75, 76
See application file for complete search history.

(56) References Cited

U.S. PATENT DOCUMENTS

| | | | |
|---|---|---|---|
| 5,378,729 A | 1/1995 | Kohn et al. |
| 5,654,301 A | 8/1997 | Kohn et al. |
| 5,773,475 A | 6/1998 | Kohn et al. |
| 5,880,158 A | 3/1999 | Kohn et al. |
| RE38,551 E | 7/2004 | Kohn et al. |
| 2005/0154043 A1 | 7/2005 | Zhai et al. |
| 2005/0261204 A1 | 11/2005 | Stohr |
| 2005/0277596 A1 | 12/2005 | Stohr |
| 2005/0288234 A1 | 12/2005 | Stohr |
| 2006/0009384 A1 | 1/2006 | Rudd et al. |
| 2006/0100157 A1 | 5/2006 | Rauschkolb-Loffler et al. |
| 2006/0154915 A1 | 7/2006 | Corte et al. |
| 2006/0252749 A1 | 11/2006 | Stohr |
| 2007/0042969 A1 | 2/2007 | Rauschkolb-Loffler et al. |
| 2007/0043120 A1 | 2/2007 | Beyreuther et al. |
| 2007/0048372 A1 | 3/2007 | Beyreuther et al. |
| 2007/0197657 A1 | 8/2007 | Beyreuther et al. |

FOREIGN PATENT DOCUMENTS

| | | |
|---|---|---|
| EP | 0592490 | 1/1998 |
| JP | 2005247841 | 9/2005 |
| WO | WO 90015069 | 12/1990 |
| WO | WO 0000463 | 1/2000 |
| WO | WO 0058346 | 10/2000 |
| WO | WO 02074297 | 9/2002 |
| WO | WO 05040355 | 5/2005 |
| WO | WO 2005053667 | 6/2005 |
| WO | WO 2005099740 | 10/2005 |
| WO | WO 2005110390 | 11/2005 |
| WO | WO 06000397 | 1/2006 |
| WO | WO 2007076306 | 7/2007 |

OTHER PUBLICATIONS

West, Anthony R., Solid State Chemistry and its Applications, Wiley, New York, 1988, pp. 358 & 365.*
International Preliminary Report on Patentability and Written Opinion issued in International Application No. PCT/US2006/062153 dated Jun. 24, 2008.
International Search Report issued in International Application No. PCT/US2006/062153 dated Jan. 6, 2007.
Co-pending U.S. Appl. No. 12/519,041, filed Jun. 12, 2009, for Use of D-Serine Derivatives for the Treatment of Anxiety Disorders.
Godunova, et al., "Asymmetric Synthesis of Amino Acids Via Catalytic Reduction of Azalactone-Substituted Acylaminoacrylic Acids", N.D. Zalinskii Institute of Organic Chemistry, translated from: Izvestiya Akademii Nauk SSR, Seriya Khimicheskaya, No. 2, 404-408, 1989.

* cited by examiner

*Primary Examiner* — Shailendra Kumar
(74) *Attorney, Agent, or Firm* — Stoel Rives LLP

(57) ABSTRACT

Compounds of Formula I are useful in the treatment of epilepsy, neuropathic pain, acute and chronic inflammatory pain, migraine, tardive dyskinesia and other related CNS disorders.

Formula I

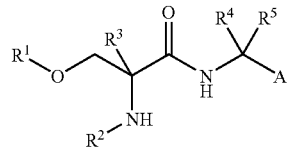

wherein:
A and $R^1$ to $R^8$ are defined in the specification.

10 Claims, No Drawings

FLUORINATED COMPOUNDS

FIELD OF THE INVENTION

The present invention relates to novel amino-acid derivatives, to processes for their preparation, to pharmaceutical composition containing them, and to their usefulness in the treatment of epilepsy, neuropathic pain, acute and chronic inflammatory pain, migraine, tardive dyskinesia and other related CNS disorders

BACKGROUND OF THE INVENTION

Epilepsy, a common neurological disorder characterized by recurrent spontaneous seizures, is considered to be a major health problem that affects approximately one to two percent of the population worldwide [Brown et. Al. *N. Engl. J. Med.,* 2001, 344, 1145-1151.]. Epilepsy also poses a considerable economic burden on society. The direct costs of epilepsy vary significantly depending on the severity of the disease and the response to treatment. Despite the considerable progress in our understanding of the pathophysiology and pharmacotherapy of seizures and epilepsy [McNamara *Nature,* 1999, 399, A15-A22.], the cellular basis of human epilepsy remains an enigma. In the absence of etiological understanding, approaches to pharmacotherapy must be directed to the control of symptoms, that is the suppression of seizures. More concerning is that current antiepileptic drugs do not halt the underlying natural progression of the disorder.

Over the years, there has been considerable success in the development of novel antiepileptic drugs (AED) along with new improved formulations. These include older 'first generation' drugs such as carbamazepine, phenobarbital, valproic acid and newer, 'second generation' drugs such as lamotrigine, vigabatrin, tiagabine, topiramate, gabapentin and levetiracetam [Brazil C W, Pedly, T A, *Ann. Rev. Med.,* 1998, 49, 135-162; McCabe P H. *Expert Opinion. Pharmacother.,* 2000, 1, 633-674]. The selection of an antiepileptic drug for treatment is predicated on its efficacy for the specific type of seizures, tolerability and safety [Regesta G, Tanganelli P, *Epilepsy Res.,* 1999, 34, 109-122; Kwan P, Brodie M J, *N. Engl. J. Med.,* 2000, 342, 314-319].

Epileptic seizures can be either generalized (generalized epileptic seizure), originating in both hemispheres of the brain simultaneously, or partial (focal seizures) originating in one or more parts of one or both hemispheres, most commonly the temporal lobe. With generalized seizures, consciousness is always impaired or lost. Consciousness may be maintained in partial seizures but partial seizures may become generalized seizures in a process referred to as secondary generalization, at which point consciousness is lost. In patients the type of epilepsy or epileptic syndrome are further classified according to features such as the type of seizure, etiology, age of onset and electroencephalogram. Epilepsy or epileptic syndromes can be either idiopathic (etiology or cause is unknown) with a presumed genetic basis or symptomatic (acquired). The known potential causes of epilepsy include brain tumors, infections, traumatic head injuries, perinatal insults, developmental malformations, cerebrovascular diseases, febrile seizures and status epilepticus [Loscher W C, *Trends Pharmacol. Sci,* 2002, 23, 113-118].

Traditionally, pharmacological strategies for treatment of epilepsy are aimed at suppressing either the initiation or the propagation of seizures rather than the underlying processes that lead to epilepsy. Some epileptic patients are unresponsive to current antiepileptic drug treatment and for this reason the major goal in epilepsy research has been to develop drugs with greater anticonvulsant efficacy and less toxicity than existing drugs [Bauer J, Reuber M, *Expert Opinion. Emerging Drugs,* 2003, 8, 457-467]. There is growing evidence that lacosamide increases seizure threshold in a variety of experimentally-induced seizures (Bailer et al. *Epilepsy Res.* 2001, 43: 11-58; Bailer et al. *Epilepsy Res.* 2004, 61: 1-48; Duncan et al. *Epilepsy Res.* 2005, 467: 81-87, Lees et al. *Neuropharmcology.* 2006: 50:98-110). Lacosamide (R-2-acetamido-N-benzyl-3-methoxy-propanamide, SPM 927) is an anticonvulsant drug that belongs to a series of functionalized-amino acids (Kohn et al. *J. Med. Chem.* 1987, 30: 567-574). Lacosamide has shown activity in a wide variety of animal models of epilepsy including the maximal electric shock (MES) test, the rat hippocampal kindling and different models of self-sustaining status epilepticus ((Kohn et al. *J. Med. Chem.* 1996, 39: 1907-1916; Kohn et al. *Bioorg. Med. Chem.* 1999; 7: 2381-2389; Kohn et al. *Bioorg. Med. Chem.* 2001; 9: 293-2708; Malawska. *Curr. Top. Med. Chem.* 2005, 5: 69-85, Kohn et al. WO9733863, EP0888289, U.S. Pat. Nos. 5,773, 475, 6,048,899, WO0000463).

A number of clinical anticonvulsants including phenyloin, carbamazepine, lamotrigine, gabapentin and pregabalin are widely utilized in the management of neuropathic pain [Collins et al. *Expert Opinion Emerging Drugs,* 2005, 10: 95-108]. Neuropathic pain results from a cascade of neurobiological events, which tend to induce electrical hyperexcitability in somatosensory conduction pathway. Since electrical hyperexcitability is also the hallmark of epileptic seizure activity, it is not surprising that anticonvulsants are among the first agents adopted in the treatment of neuropathic pain and remain the first option in clinical use. In addition to its anticonvulsive properties, Lacosamide has demonstrated antinociceptive activity in animal models of neuropathic pain and models of acute and chronic inflammatory pain [Stohr et al. *Eur. J. Pain* 2006, 10: 241-249; Selves et al. WO02074784; Stohr. WO 2005053667].

In recent years pain management has become an area of increasing focus in the medical profession, partly due to the growing elderly population, issues surrounding quality of life and the growing numbers of patients reportedly suffering from pain. Pain is both a sensory and emotional experience, and is generally associated with tissue damage or inflammation. Typically, pain is divided into two general categories—acute pain and chronic pain. Both differ in their etiology, pathophysiology, diagnosis, and most importantly treatment.

Acute pain is short term, and is typically of readily identifiable cause. Patients suffering from acute pain typically respond well to medications. In contrast, chronic pain—medically defined as pain that lasts for 3-6 months or longer, is often not associated with an obvious injury; indeed, patients can suffer from protracted pain that persists for months or years after the initial insult. Whilst acute pain is generally favorably treated with medications, chronic pain is often much more difficult to treat, generally requiring expert care.

According to the American Chronic Pain Association, over 86 million Americans suffer from chronic pain, and the management of chronic pain has long been recognized as an unmet clinical need. Most chronic pain is neuropathic in nature (also referred to as neuralgia). Neuropathic pain can, for instance, manifest itself as burning, stabbing, and shock-like sensations.

Unfortunately, neuropathic pain management is at best inconsistent, and often ineffective. This is in part due to the subjective nature of the pain, but also due to poor diagnosis, especially when the chronic pain is not clearly associated with a nerve injury or other insult. Moreover, few, if any, ethical drugs have been prospectively developed for the treatment of chronic pain. Instead, the current medications used to treat chronic pain are "borrowed" from other diseases, most commonly antiepileptic drugs and antidepressants.

Current first-line treatments for chronic pain include opioids, analgesics such as gabapentin, and tricyclic antidepressants. When opioids are administered over prolonged periods, undesirable side effects such as drug tolerance, chemical dependency and even physiological addiction can occur. Of treatment remedies currently available for chronic pain, at best approximately 30% are effective in significantly diminishing the pain, and even these may lose their efficiency over time. Although numerous pharmacological agents are available for the treatment of neuropathic pain, a definitive therapy has remained elusive.

In instances in which treatment with a single agent proves to be unsuccessful, combination therapy is often then explored as a second line treatment. For example, such combination therapy may employ administration of an opioid agent with an adjuvant analgesic, although the relative doses of each are often subject to prolonged trial and error periods. Often, triple drug therapy is necessary. Such therapy generally involves a combination of tricyclic antidepressants, anticonvulsants and a systemic local anesthetic. Patient compliance drops significantly, however, when treatment requires the administration of multiple pharmacologic agents. Recently, researchers reported the use of a combination of morphine and gabapentin in a randomized study for controlling nerve pain (Gilron, I., et al., N. Eng. J. Med., 352:1281-82, 2005).

It is not only important to consider overall pain relief, but also the type of pain relief. For example, chronic pain is typically viewed as allodynia or hyperalgesia. Allodynia is pain sensation from a stimulus which is not normally painful. This allodynia is typically caused by a physical stimulus and is thus referred to as tactile or mechanical allodynia. Hyperalgesia is an exaggerated sensation form a stimulus which is normally painful. The hyperalgesia can occur from a variety of stimuli but, commonly, a patient's reaction to hot or cold stimuli is reported. Importantly, physicians often report that the current drugs are most effective at relieving hyperalgesia, although most patients present allodynia, particularly mechanical allodynia.

In addition to poor and/or inconsistent efficacy, these medications have several other undesirable properties such as adverse events, duration of action, and complicated dosing and titration regimens.

The most common side-effect of the non-opiate drugs is sedation or somnolence. Based upon data from the package inserts for these drugs, as many as 20-30% of patients experience sedation. As mentioned above, the population greatest at risk for chronic pain is the elderly. For the elderly, experiencing significant and persistent sedation poses other risks, mainly locomotor function impairment. Such locomotors function impairment can lead to falls and the inability to perform many daily functions such as driving.

The duration of action is also a limitation for the most of the leading therapies. This is particularly important as pain, and especially nighttime pain, can lead to depression, insomnia and other factors which impact the patients' overall quality of life. A recent study suggests that patients with chronic pain and concurrent major depression and insomnia report the highest levels of pain-related impairment. This study also found that insomnia in the absence of major depression is also associated with increased pain and distress. (Wilson et al., Clin. J. Pain 2002, 18: 77-83.) Therefore, achieving pain relief with sufficient duration to achieve relief through the night is an important factor for neuropathic pain drugs. Pain-relief drugs such as gabapentin are taken once or more during the night to achieve pain relief, thus disturbing sleep and exacerbating the patient's overall quality of life.

Neuropathic pain (NP) is generally thought of a maladaptive chronic condition in which pain originates from damaged nerves, often yielding pain that is out of proportion to the extent of any injury. Damage can occur from a physical injury such as trauma or from chemical injury such as chemotherapeutics (e.g. paclitaxel). Neuropathic pain of this type is an important component of a number of syndromes of varying etiologies whose common characteristic is the development of a prolonged and profound pain state. Among these conditions are spinal cord injury, post-herpetic neuralgia, diabetic neuropathy, phantom limb pain, stump/neuroma pain, post-ischemic pain (stroke), fibromyalgia, complex regional pain syndrome (CRPS), chemotherapy-induced neuropathic pain, vertebral disk rapture, trigeminal neuralgia and others.

Recently, however, it has been recognized that neuropathic pain can also manifest itself in the absence of an identifiable nerve injury. These indications include AIDS and mirror image pain. The lack of any nerve injury but unmistakable chronic pain has led to increased interest in the role of glial cells in the maintenance of the neuropathic pain state (Watkins L R; Maier S F 2004, Drug Disc. Today: Ther. Strategies 1: 83-88; Watkins L R, Maier S F Nat Rev Drug Discovery 2003, 2:973-985). More specifically, recent research has demonstrated that glial cells enhance the release of neurotransmitters which relay pain information to the spinal cord and, even more strikingly, release substances which increase the excitability of pain-responsive neurons in the spinal cord. These substances, called pro-inflammatory cytokines, create and maintain exaggerated or pathological pain responses (Wieseler-Frank et al. Neurosignals 2005, 14: 166-174). Blocking the activation of glial cells reduces pro-inflammatory cytokines and reverses pathological pain. To date, no therapeutics have been approved which have a putative glial cell-attenuation mechanism for the treatment of neuropathic pain. Molecules which are glial cell-attenuators may play an important role in the treatment of neuropathic pain.

In light of the above shortcomings in current approaches for treating chronic pain there exists a need for improved compositions and methods for treating pain, particularly neuropathic pain and its associated symptoms and, more specifically, neuropathic pain associated with certain conditions such as fibromyalgia, among others. Such approaches should ideally overcome one or more of the problems associated with existing methods for treating chronic pain. The present invention meets these needs.

At present no analgesic exists which is highly potent in various pain syndromes. Different mechanisms leading to inflammatory or neuropathic pain make it difficult to identify compounds which have general analgesic activity. We are only at the beginning of understanding the mechanisms behind different pain syndromes like cancer pain (e.g. tumor-induced bone cancer pain), chemotherapy-induced pain or nucleoside-induced pain, all of which seem to have various molecular origins. Antidepressants, anticonvulsants or opioids, which describe groups of compounds used in pain treatment, do not have a common pattern regarding their efficacy in treatment of pain syndromes. This makes it difficult to predict the activity of new compounds in the various pain syndromes and demands a detailed characterization in multiple models of pain in animals.

Neuropathic pain after injury or dysfunction to the peripheral or central nervous system remains a difficult clinical problem for which effective treatments are lacking (Bennett, 1994, *Ann. Neurol.* 35: S38-S41; Murphy and Reid, 2001 Ref.?). Anticonvulsants are used for the management of some forms or neuropathic pain (Sindrup S H; Jenssen T S, Pain 1999, 389-400; Jensen, 2002, *Eur. J. Pain* 6: 61-68).

Bone is the third most common site of metastasis after lung and liver, and is the primary site of metastatic disease in patients with breast, prostate and lung cancer. The bone lesions that result from metastatic disease also cause severe bone pain, which is a major clinical problem in cancer patients. This type of pain is difficult to treat due to its intermittent, progressive nature and its aggravation by movement. The predominant symptom in this model of pain is mechanical allodynia. Thermal hyperalgesia and mechanical hyperalgesia have also been demonstrated as measured by the weight bearing difference in the two hind limbs (Medhurst et al., 2002, *Pain* 96: 129-140). Treatment of bone pain in human patients is largely limited to the use of opioids. However, the efficacy of potent opioids is minimal, and effective doses produce a range of debilitating side effects. Consequently, there is a clinical need for new therapies which can be used to prevent, treat and alleviate tumor-induced bone pain. Candidate therapies for treatment of tumor-induced bone pain can be evaluated using a rat model, as the rat is superior for testing behavioral responses to pain stimuli. One such model involves the injection of rat mammary gland carcinoma cells into the marrow space of the proximal tibia, using an endpoint of pain assessment (Medhurst et al., 2002, *Pain* 96: 129-140), which was performed on days 7 to 15 following tumor implantation.

Chemotherapy-induced pain is a form of neuropathic pain associated with neurotoxic drugs such as vinca alkaloids (e.g. vincristine) and is characterized by painful paresthesias and dysesthesias. The clinical antineoplastic efficacy of vincristine is limited by the development of a mixed sensorimotor neuropathy (Casey et al., *Brain.* 1973, 96: 69-86; Tanner et al., *J Neurosci.* 1998, 18: 6480-6491) which appears to occur in two major stages (Weiss et al., *N Engl J. Med.* 1974, 291:127-133). In the early stage, peripheral axons are damaged by vincristine and the principal symptoms are paresthesias and dysesthesias. In the later stage, which occurs more frequently when higher doses are given for longer periods of time, axons are lost and the principal clinical finding is loss of motor function. The described vincristine rat model seems to reflect the early stage of vincristine-induced chemotherapeutic neuropathy. Whilst the underlying mechanism is not fully understood as yet, it has been described as causing a disorganization of the axonal microtubule cytoskeleton, as well as an increase in the caliber of unmyelinated sensory axons (Quasthoff S, Hartung H P *J. Neurol.* 2002, 249: 9-17). These results demonstrate that changes in microtubule structure in nociceptive sensory neurons accompany vincristine-induced hyperalgesia.

Painful peripheral neuropathy induced by nucleoside analogues is becoming recognized and an important source of morbidity in human immunodeficiency virus (HIV) infected individuals (Cohen, 2002). This severely debilitating side-effect may force abbreviation or even discontinuation of AIDS (acquired immunodeficiency syndrome) therapy (Yatvin et al., 1999). This neuropathy is characterized by a sudden onset of intense burning discomfort in both feet sparing the hands at about the $10^{th}$ week of treatment, and which reaches severe intensity over a period of days (Dubinsky et al., 1989). The biochemical mechanism underlying this side-effect remains to be clearly established, although mitochondrial toxicity has been reported to contribute to its development. Recently, it has been reported that treatment of rats with antiretroviral nucleoside analogue AIDS therapy drugs ddC (2',3'-dideoxycytidine), ddI (2',3'-dideoxyinsine) or d4T (2',3'-didehydro-3'-deoxythymidine) produces enhanced nociception in the rat (Joseph et al., 2004). The mechanism involved appears different from that of other models of metabolic or toxic painful peripheral neuropathy, as anti-hyperalgesic drugs are effective in these models. Inhibitors of protein kinase A, protein kinase C, protein kinase G, p42/p44-mitogen-activated protein kinase (ERK1/2) and nitric oxide synthase have no effect on peripheral neuropathies, and had no effect on nucleoside reverse transcriptase inhibitor-induced hypersensitivity. Intracellular calcium modulators (TMB-8 and Quin-2) are the only agents capable of reversing this hypersensitivity of intoxicated animals strongly suggests the role of intracellular calcium in this type of neuropathic pain.

Chemotherapy, e.g. treatment with vinca alkaloids like vincristine or with taxol, suramin, cisplatin, carboplatin or oxaliplatin is used for the treatment of cancer and HIV patients. Additionally, HIV or/and tumor patients are also treated with antiretrovirals or antivirals. Recently, Lacosamide has been shown to be potentially useful for treating tumor pain, in particular bone cancer pain, for treating chemotherapy-induced pain and for treating nucleoside-induced pain.

The pathophysiology of migraine is thought to involve activation of trigeminal afferents [Goadsby et al *N. Eng. J. Med.* 2002, 346: 95-108] The trigeminal sensory nerve fibers that innervate cranial structures contain the neuropeptide calcitonin gene-related peptide (CGRP). Activation of Aδ-trigeminal nerve fibres causes the release of CGRP and dilation of dural arteries in animals, whilst CGRP levels in the blood plasma of migraineurs are increased during a migraine episode. Intravenous injection of CGRP causes a dull headache and subsequent migraine in humans and dural blood vessel dilation in rats. Recent clinical evidence suggests that blockade of CGRP has a potent acute antimigraine effect [Olesen et al. *N. Eng. J. Med.* 2004, 350: 1104-1110].

Interestingly, there is also strong evidence that Cortical Spreading Depression (CSD) serves as an initiating event for migraine visual aura and pain [Moskowitz et al. *Nat. Med.* 2002, 8:136-142]. CSD is a transient suppression of cortical activity, which starts locally and spreads throughout the tissue. CSD usually leads to trigeminal activation and, putatively, to the release of CGRP. Lacosamide has been shown to suppress CSD and to reduce CSD-induced release of CGRP and is therefore of potential importance in the clinical treatment of acute migraine, the prophylactic treatment of migraine and for the treatment of other forms of chronic headache and/or CSD-associated disorder [Stohr et al. WO 2005099740]

More recently lacosamide has demonstrated efficacy in the reserpine-induced vacuous chewing movement, a mouse model of tardive dyskinesia, suggesting the potential clinical utility of this compound in the prevention, alleviation and/or treatment of dyskinesia [Stohr et al. WO 2005110390]. Dyskinesia is a common complication of L-DOPA pharmacotherapy in Parkinson's disease, and is thought to depend on abnormal cell signaling in the basal ganglia [Cenci et al. *Exp. Neurol.* 2005, 194: 66-75].

Although lacosamide displays potential utility in a wide variety of CNS disorders the methoxy group undergoes significant demethylation to the O-desmethyl metabolite. As a result, any attempt to block this demethylation pathway could improve the overall clinical profile.

It has now been found that a novel class of fluorinated serine derivatives is useful in the treatment of epilepsy, neuropathic pain, acute and chronic inflammatory pain, migraine, tardive dyskinesia and other related CNS disorders.

SUMMARY OF THE INVENTION

We have discovered that compounds of Formula I:

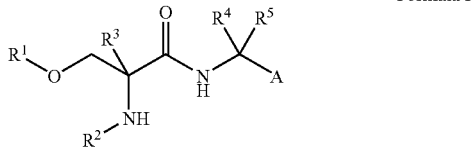

Formula I wherein:
A is selected from the group consisting of aryl and heteroaryl, optionally substituted with one or more independently-selected groups $R^8$;
$R^1$ is a haloalkyl group;
$R^2$ is selected from the group consisting of H, $C(O)R^6$, $C(O)OR^6$, $SO_2R^6$ and $C(O)NR^6R^7$;
$R^3$, $R^4$ and $R^5$ are independently selected from the group consisting of H and alkyl;
$R^6$ and $R^7$ are independently selected from the group consisting of H and alkyl; and
$R^8$ is selected from the group consisting of OH, CN, halo, alkyl, alkoxy, haloalkyl, haloalkoxy, $C(O)R^6$, $C(O)OR^6$, $SO_2R^6$ and $C(O)NR^6R^7$;
are useful in the treatment of epilepsy, neuropathic pain, acute and chronic inflammatory pain, migraine, tardive dyskinesia and other related CNS disorders.

Another embodiment of the invention provides a composition comprising a compound of Formula I and a carrier; in a further aspect of the invention the carrier is a pharmaceutically-acceptable carrier.

In another aspect of the invention there are provided compositions containing the present compounds in amounts for pharmaceutical use to treat medical conditions such as epilepsy, neuropathic pain, acute and chronic inflammatory pain, migraine, tardive dyskinesia and other related CNS disorders; such compositions comprise a compound of Formula I in association with one or more pharmaceutically acceptable diluents, excipients and/or inert carriers.

Definitions

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight- or branched-chain hydrocarbon radical having from one to six carbon atoms, and includes methyl, ethyl, propyl, isopropyl, t-butyl and the like.

The term "alkoxy" as used herein means a straight- or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "haloalkyl" as used herein means an alkyl group in which at least one H atom has been replaced by a halo atom, and includes groups such as $CF_3$, $CH_2Br$ and the like.

The term "haloalkoxy" as used herein means an alkoxy group in which at least one H atom has been replaced by a halo atom, and includes groups such as $OCF_3$, $OCH_2Br$ and the like.

The term "aryl" as used herein means an aromatic group having five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound of Formula I which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

DETAILED DESCRIPTION OF THE INVENTION

One embodiment of the invention provides compounds of Formula I, or a salt or solvate thereof.

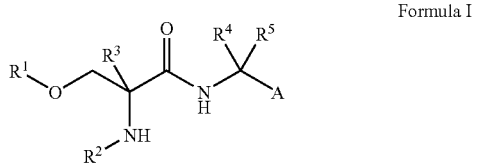

Formula I wherein:
A is selected from the group consisting of aryl and heteroaryl, optionally substituted with one or more independently-selected groups $R^8$;
$R^1$ is a haloalkyl group;
$R^2$ is selected from the group consisting of $C(O)R^6$, $C(O)OR^6$, $SO_2R^6$ and $C(O)NR^6R^7$;
$R^3$, $R^4$ and $R^5$ are independently selected from the group consisting of H and alkyl;
$R^6$ and $R^7$ are independently selected from the group consisting of H and alkyl; and
$R^8$ is selected from the group consisting of OH, CN, halo, alkyl, alkoxy, haloalkyl, haloalkoxy, $C(O)R^6$, $C(O)OR^6$, $SO_2R^6$ and $C(O)NR^6R^7$;

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate or chemical or enzymatic resolution methodology, by synthesis from optically active starting materials or by asymmetric synthesis based on the procedures described thereafter.

It will also be understood by those of skill in the art that certain compounds of the present invention may exist in solvated, for example hydrated, as well as unsolvated forms. It will further be understood that the present invention encompasses all such solvated forms of the compounds of Formula I.

Within the scope of the invention are also salts of the compounds of Formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of Formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the compounds 1 to 30 as illustrated in the following table, their pharmaceutically acceptable salts, hydrates, solvates, optical isomers, and combinations thereof:

| Compound | Structure | Name |
|---|---|---|
| 1 | 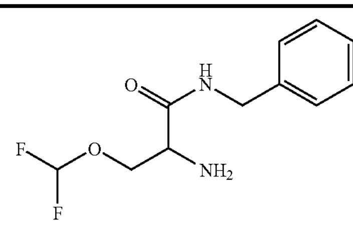 | 2-Amino-N-benzyl-3-(difluoromethoxy) propanamide |
| 2 | 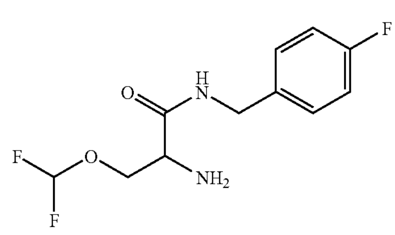 | 2-Amino-3-difluoromethoxy-N-(4-fluorobenzyl) propionamide |

| Compound | Structure | Name |
|---|---|---|
| 3 | 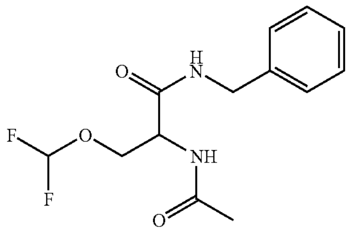 | 2-(Acetylamino)-N-benzyl-3-(difluoro-methoxy)propanamide |
| 4 | 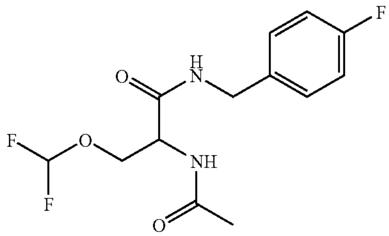 | 2-(Acetylamino)-3-difluoromethoxy)-N-(4-fluoro-benzyl)propanamide |
| 5 | 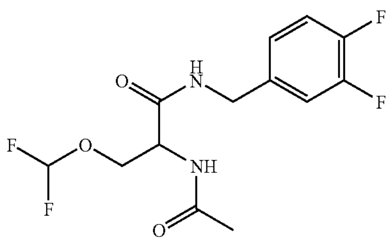 | 2-(Acetylamino)-N-(3,4-difluorobenzyl)-3-(difluoromethoxy)propanamide |
| 6 | 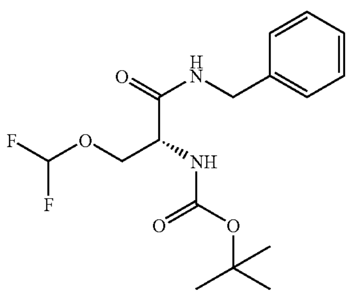 | tert-Butyl {(1R)-2-(benzylamino)-1-[(difluoromethoxy)methyl]-2-oxoethyl} carbamate |
| 7 | 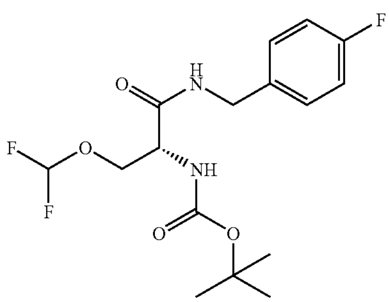 | tert-Butyl {(1R)-1-[(difluoromethoxy)methyl]-2-[(4-fluorobenzyl)amino]-2-oxoethyl}carbamate |
| 8 | 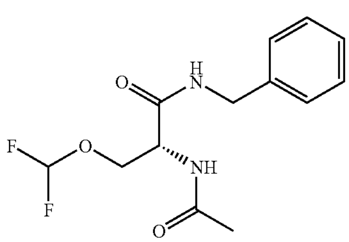 | (2R)-2-(Acetylamino)-N-benzyl-3-(difluoro-methoxy)propanamide |

-continued

| Compound | Structure | Name |
|---|---|---|
| 9 | 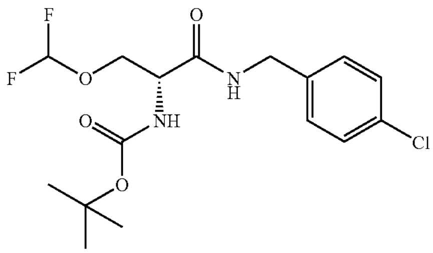 | tert-butyl {(1R)-1-[(difluoromethoxy)methyl]-2-[(3-fluoro-benzyl amino]-2-oxoethyl}carbamate |
| 10 | 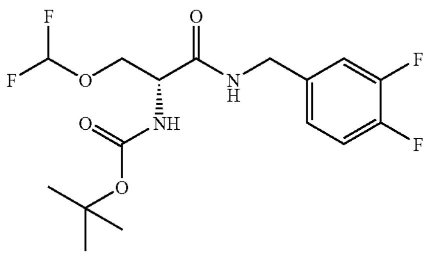 | tert-butyl {(1R)-1-[(difluoromethoxy)methyl]-2-[(3,4-difluorobenzyl)amino]-2-oxoethyl}carbamate |
| 11 | 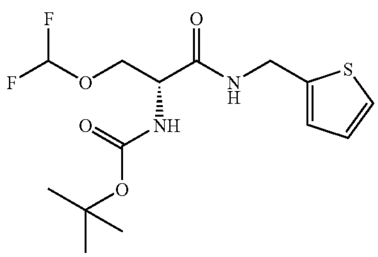 | Tert-butyl {(1R)-1-[(difluoromethoxy)methyl]-2-oxo-2-[(2-thienylmethyl)amino]ethyl}carbamate |
| 12 | 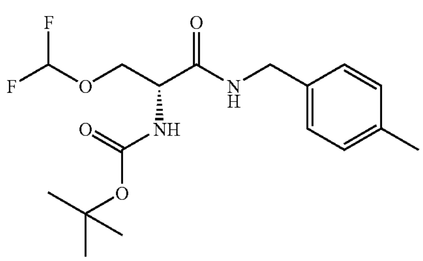 | tert-butyl {(1R)-1-[(difluoromethoxy)methyl]-2-[(4-methyl-benzyl)amino]-2-oxoethyl}carbamate |
| 13 | 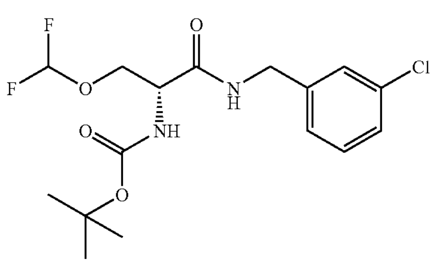 | tert-butyl {(1R)-2-[(3-chlorobenzyl)amino]-1-[(difluoro-methoxy)methyl]-2-oxoethyl}carbamate |
| 14 | 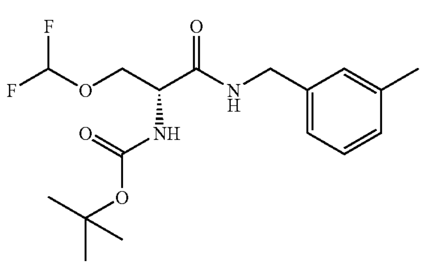 | tert-butyl {(1R)-2-[(3-methylbenzyl)amino]-1-[(difluoro-methoxy)methyl]-2-oxoethyl}carbamate |

-continued

| Compound | Structure | Name |
|---|---|---|
| 15 | 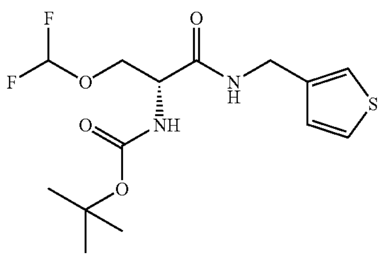 | tert-butyl {(1R)-1-[(difluoromethoxy)methyl]-2-oxo-2-[(3-thienylmethyl)amino]ethyl}carbamate |
| 16 | 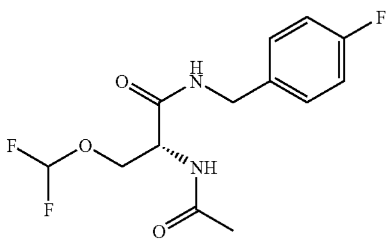 | (2R)-2-(Acetylamino)-3-(difluoromethoxy)-N-(4-fluorobenzyl)propanamide |
| 17 | 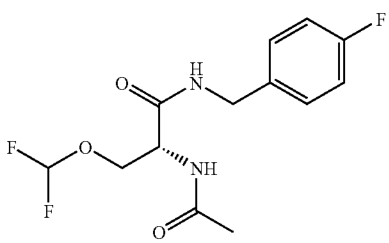 | (2R)-2-(Acetylammino)-3-(difluoromethoxy)-N-(4-fluorobenzyl)propanamide |
| 18 | 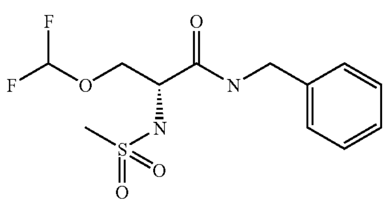 | (2R)-N-benzyl-3-(difluoromethoxy)-2-[(methyl-sulfonyl)amino]propanamide |
| 19 | 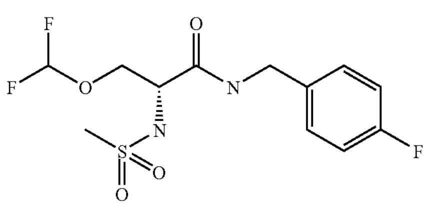 | (2R)-3-(difluoromethoxy)-N-(4-fluorobenzyl)-2-[(methylsulfonyl)amino]propanamide |
| 20 | 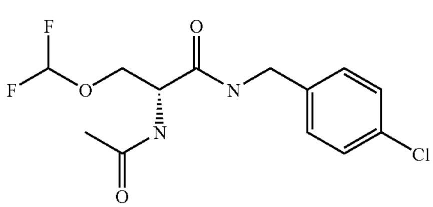 | (2R)-2-(acetylamino)-N-(4-chlorobenzyl)-3-(difluoromethoxy)propanamide |
| 21 | 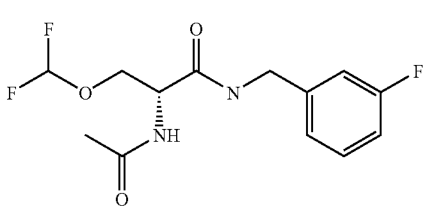 | (2R)-2-(acetylamino)-3-(difluoromethoxy)-N-(3-fluorobenzyl)propanamide |

-continued

| Compound | Structure | Name |
|---|---|---|
| 22 | 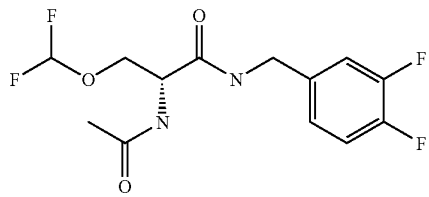 | (2R)-2-(acetylamino)-N-(3,4-difluorobenzyl)-3-(difluoromethoxy)propanamide |
| 23 | 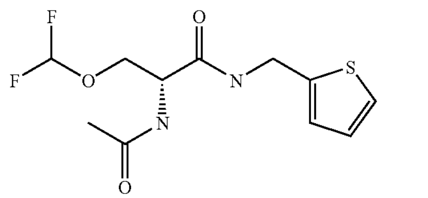 | (2R)-2-(acetylamino)-3-(difluoromethoxy)-N-(2-thienylmethyl)propanamide |
| 24 | 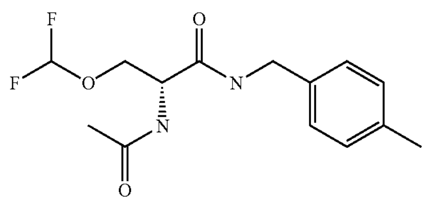 | (2R)-2-(acetylamino)-3-(difluoromethoxy)-N-(4-methylbenzyl)propanamide |
| 25 | 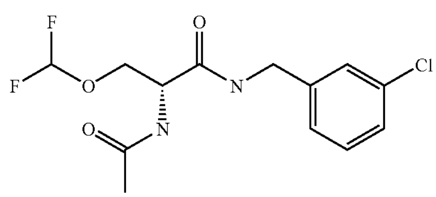 | (2R)-2-(acetylamino)-N-(3-chlorobenzyl)-3-(difluoromethoxy)propanamide |
| 26 | 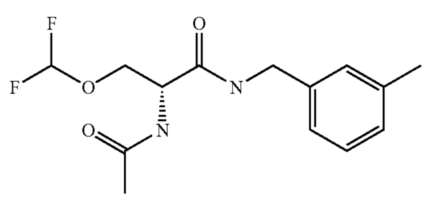 | (2R)-2-(acetylamino)-3-(difluoromethoxy)-N-(3-methylbenzyl)propanamide |
| 27 | 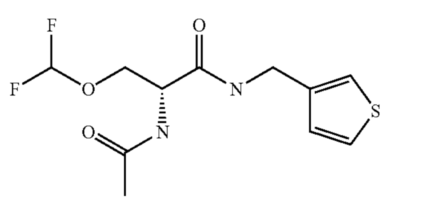 | (2R)-2-(acetylamino)-3-(difluoromethoxy)-N-(3-thienylmethyl)propanamide |
| 28 | 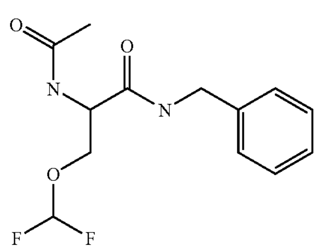 | 2-Acetylamino-N-benzyl-3-difluoromethoxy-propionamide |

| Compound | Structure | Name |
|---|---|---|
| 29 | 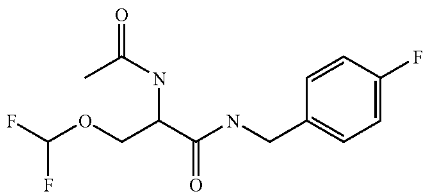 | 2-Acetylamino-3-difluoromethoxy-N-(4-fluoro-benzyl)-propionamide |
| 30 | 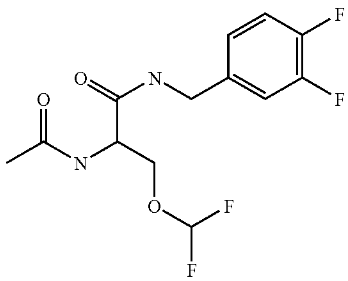 | 2-Acetylamino-N-(3,4-difluoro-benzyl)-3-difluoromethoxy-propionamide |

The introduction of the fluorine atom into molecules brings about dramatic changes in the physical and chemical properties of the parent molecules, and sometimes results in the enhancement of pharmacokinetic properties and biological activities. The unique properties of the fluorine atom include it small size, low polarizability, high electronegativity and its ability to form strong bonds with carbon. Recently, bioactive compounds containing trifluoromethoxy, difluoromethoxy and fluoromethoxy groups have attracted great interest. Replacement of hydrogen atoms can sometimes result in improved thermal and metabolic stability. Improved metabolic stability is usually a desirable feature since the possibility exists that in vivo decomposition may produce toxic effects.

The geminal combination of an alkoxyl or aryloxy group with a fluorine atom offers the possibility of bonding/non-bonding resonance, which can be formally expressed by the superposition of a covalent and ionic limiting structure. This phenomenon, which reveal itself as a lengthening and weakening of the carbon-halogen bond and a shortening and strengthening of the carbon-oxygen bond is widely known as the generalized anomeric effect [Schlosser et al *Chem. Rev.* 2005, 105: 827-856].

Non-Medical Use

In addition to their use in therapeutic medicine, the compounds of Formula I, as well as salts and hydrates of such compounds, are useful as pharmacological tools in the development and standardization of in vitro and in vivo test systems for the evaluation of the effects of potentiators of mGluR related activity in laboratory animals such as cats, dogs, rabbits, monkeys, rats and mice, as part of the search for new therapeutic agents.

Preparation of Compounds

Fluoro methyl ether derivatives [Manson et al *J. Am. Chem. Soc.* 1956, 78: 1682] can be obtained from the corresponding chloro analogs by nucleophilic substitution with KF and the chloromethyl ethers are readily accessible [Hayashi et al *Bull. Chem. Soc. Jpn* 1980, 53: 2701; Marvel et al *Org. Syn. Coll. Vol.* 1941, 1: 369; Davis et al *Org. Synth.* 1967, 47: 123; Sharma et al *J. Org. Chem.* 1968, 33: 3335; Hayami et al *Bull. Chem. Soc. Jpn* 1971, 44: 3091]. The O-α-fluoro alkyl ethers can be most conveniently prepared from the reaction of the vinyl ether with N-Bromosuccinimide (NBS) in the presence of HF followed by reductive debromination.

O-α-fluoro alkyl ethers

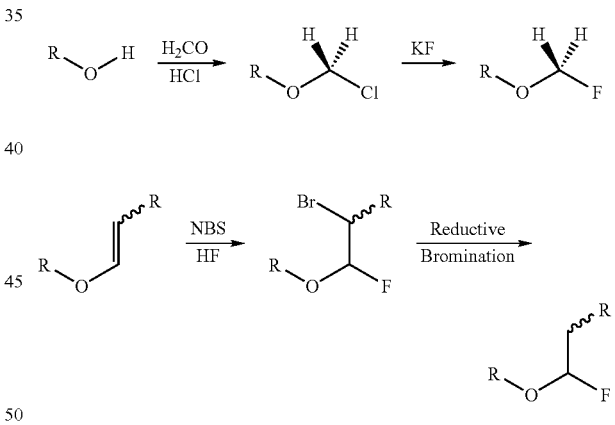

The O-α,α-difluoro alkyl ethers can be prepared by electrophilic reactions of the appropriate alkoxide anion with Chlorodifluoromethylation in the presence of base [Clark et al *J. Am. Chem. Soc.* 1955, 77: 6618; Miller et al *J. Org. Chem.* 1960, 25: 2009, Sharma et al *J. Fluorine. Chem.* 1988, 41: 247]; difluorocarbene [Naumann et al *J. Fluorine. Chem.* 1994, 67: 91; Naumann et al *Liebigs. Ann.* 1995, 1717-1719] and difluoromethylcarbocation equivalent [Uneyama et al *Tetrahedron Lett.* 1993, 34: 1311; Uneyama et al *J. Org. Chem.* 1995, 60: 370].

Alternatively, the difluoromethyl ethers could also be accessible by sulfur tetrafluoride mediated fluorodeoxygenation of formates [Sheppard et al *J. Org. Chem.* 1964, 29: 1] or from the treatment of the alcohol with Iododifluoromethyl phenyl sulphone to give the corresponding ether which can undergo reductive desulphonylation [Olah et al Org. Lett. 2005, 6: 4315].

O-α,α-difluoro alkyl ethers

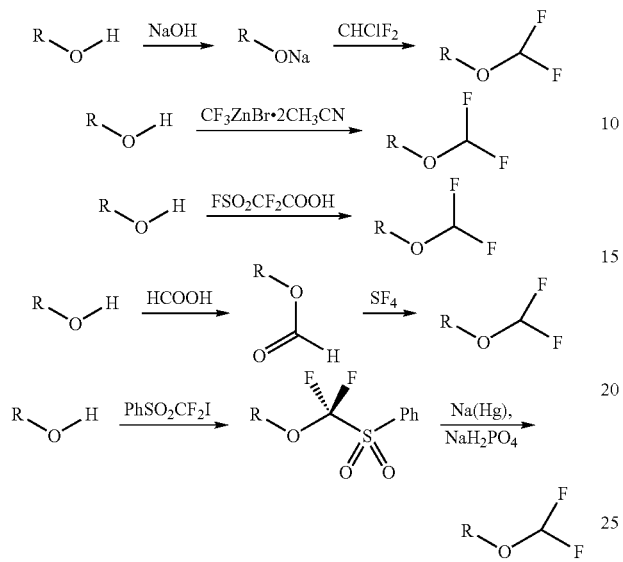

The O-α,α,α-trifluoro alkyl ethers can be prepared by a recently disclosed fluorodesulfurization involving the treatment of dithiocarbonates (xanthogenates) with excess HF/Pyridine and 1,3-dibromo-5,5-dimethylhydantoin. The trifluoromethyl ethers are usually formed in moderate to excellent yield [Kanie et al Bull. Chem. Soc. Jpn 2000, 73: 471; Kanie et al Adv. Synth. Catal. 2001, 343: 235].

O-α,α,α-trifluoro alkyl ethers

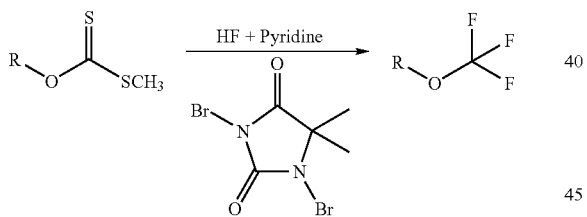

Alkyl trifluoromethyl ethers can also be prepared by (1) treating alkylfluoroformates with SF4 [Sheppard et al J. Org. Chem. 1964, 29: 11]; (2) trifluoromethyl transfer from O-(trifluoromethyl) dibenzofuranium tetrafluoroborate [Umemoto, T. Chem. Rev. 1996, 96: 1757] and (3) and the addition of trifluoromethyl hypofluorite (FOCF3) to alkenes [Rozen, S. Chem. Rev. 1996, 96: 1717].

As referred to above, individual compounds of Formula I may be prepared according to various methods described above utilizing the appropriately protected series as the representative alcohol precursor.

Synthesis of difluoromethoxy compounds of Formula I

Compound of Formula I can be prepared as shown in Scheme 1, below, or by variations apparent to those of skill in medicinal chemistry as needed to vary A, $R^1$, $R^2$, $R^3$, $R^4$, $R^5$, $R^6$, $R^7$ and $R^8$.

The commercially available amino acid serine 1 can first be N-protected with G1 and G2 (e.g. G1=G2 is Benzyl) and the resulting intermediate can then be easily transformed into the ester precursor 2. The corresponding ester 3 (benzyl ester derivative shown) can be converted to the difluoromethoxy derivative utilizing difluoromethylating agents such as $FSO_2CF_2COOH$ or $CF_3ZnBr\cdot2CH_3CN$, which can then be subjected to deprotection conditions (e.g. shown is hydrogenation) to afford the difluoromethoxyserine precursor 4. Acylation of 4, utilizing procedures established in the art, followed by amide bond formation using known coupling procedures provides the difluoromethoxy derivatives of Formula I (A).

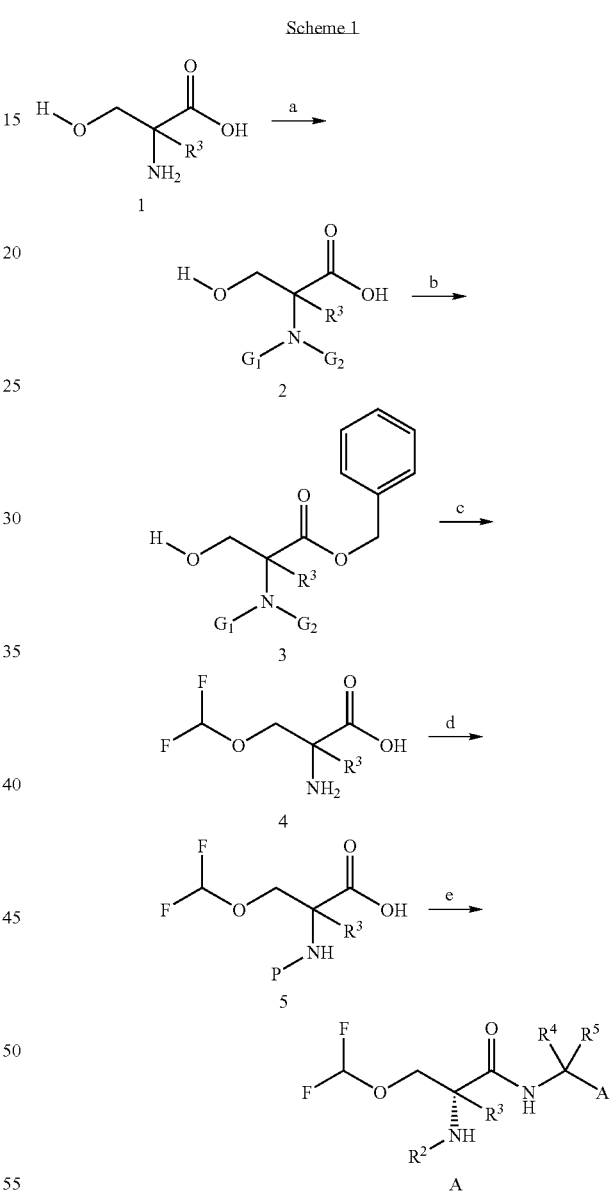

a PhCH$_2$Br, K$_2$CO$_3$, CH$_3$CN;
b PhCH$_2$Br or MeI, K$_2$CO$_3$, CH$_3$CN;
c i. FSO$_2$CF$_2$COOH, Na$_2$SO$_4$, CH$_2$CN or
  CF$_3$ZnBr·2CH$_3$CN/CH$_2$Cl$_2$; ii. H$_2$, Pd, solvent;
d Boc$_2$O or Ac$_2$O (P=Boc or Ac)
e i. ClCOOCH$_2$CH(CH$_3$)$_2$, Et$_3$N, THF ii. AcR$^4$R$^5$NH$_2$ An alternative synthesis of compound of Formula I wherein $R^1$ is CHF$_2$ utilizes the difluoro (phenylseleno)-methylcarbocation equivalent (obtained via a Pummerer rearrangement of difluoromethyl phenyl selenoxide) and the cyclic ether oxetane. The reaction of difluoromethyl phenyl selenoxide 6 [Uneyama et al Tetrahedron Lett. 1993, 34:

1311; Uneyama et al *J. Org. Chem.* 1995, 60: 370] with oxetane 7 in acetic anhydride should give the intermediate 8 which can undergo reductive deselenation to afford 9. Hydrolysis of 9 followed by oxidation should provide the difluoromethoxy acid 10. Activation of acid 10 should give the oxazolidinones 11, which undergoes α-azidation to afford 11. Staudinger reduction of 11 and subsequent acetylation with acetic anhydride should give 12. Treatment of 12 with the amine should provide the difluoromethoxy derivatives of Formula I, as shown in Scheme 2, below. Variations will be apparent to those of skill in medicinal chemistry as needed to vary A, $R^1$, $R^2$, $R^3$, $R^4$, $R^5$, $R^6$, $R^7$ and $R^8$.

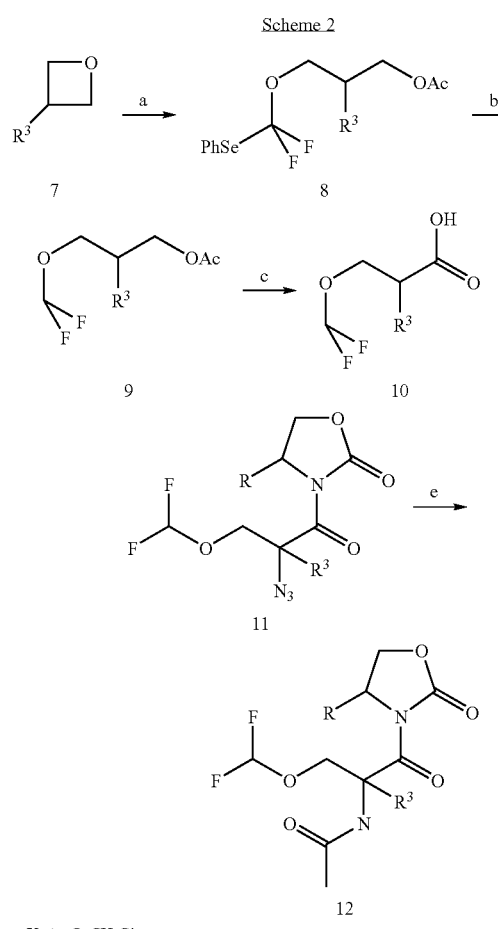

a X, $Ac_2O$, $CH_2Cl_2$
b AIBN, $R_3SnH$
c i. $K_2CO_3$, MeOH ii. Oxidation
d 2•Pivaloyl chloride, $Et_3N$, Y ii $KN(SiMe_3)_2$, Trisyl Azide
e $Ph_3P$, $H_2O$, $Ac_2O$
f $AcR^4R^5NH_2$,

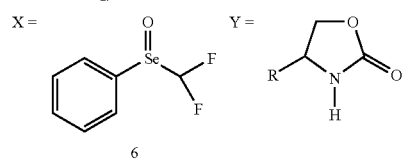

Another embodiment of the invention provides a method for preparing a compound of the invention according to Scheme 3, below, or by variations apparent to those of skill in medicinal chemistry as needed to vary A, $R^1$, $R^2$, $R^3$, $R^4$, $R^5$, $R^6$, $R^7$ and $R^8$:

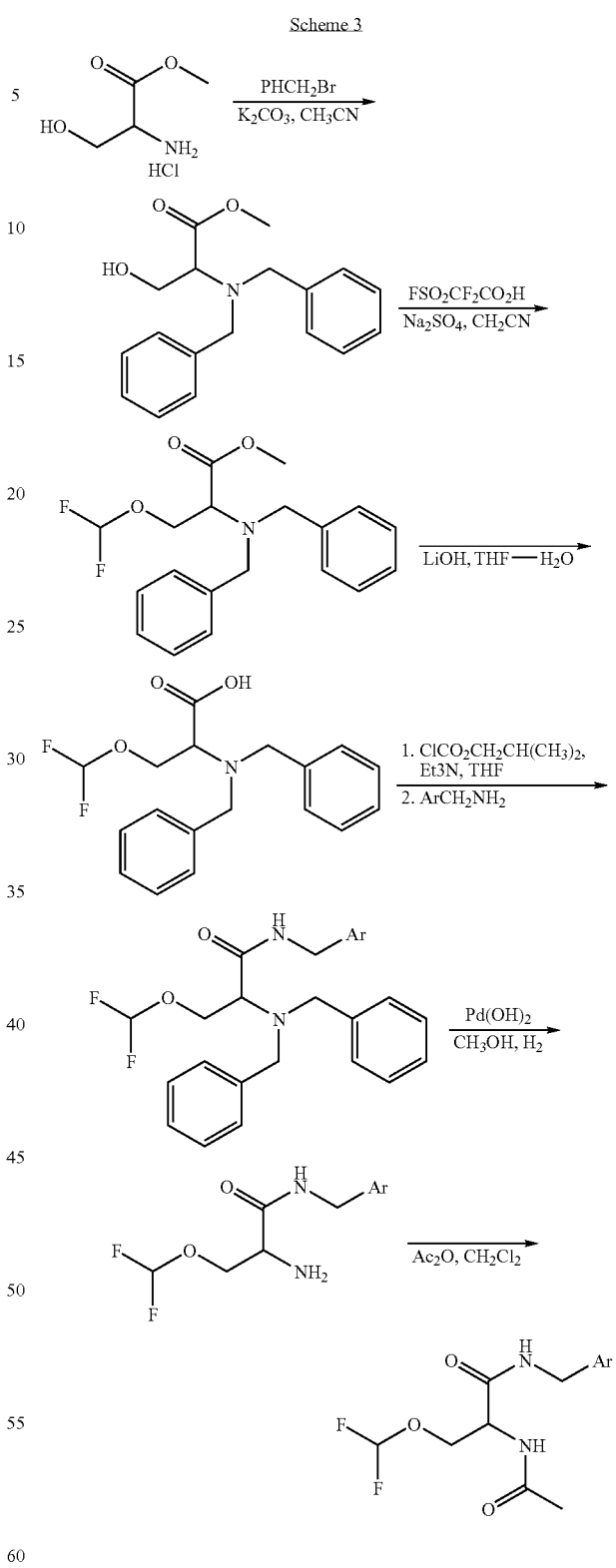

A further embodiment of the invention provides a method for preparing a compound of the invention according to Scheme 4, below, or by variations apparent to those of skill in medicinal chemistry as needed to vary A, $R^1$, $R^2$, $R^3$, $R^4$, $R^5$, $R^6$, $R^7$ and $R^8$:

Scheme 4

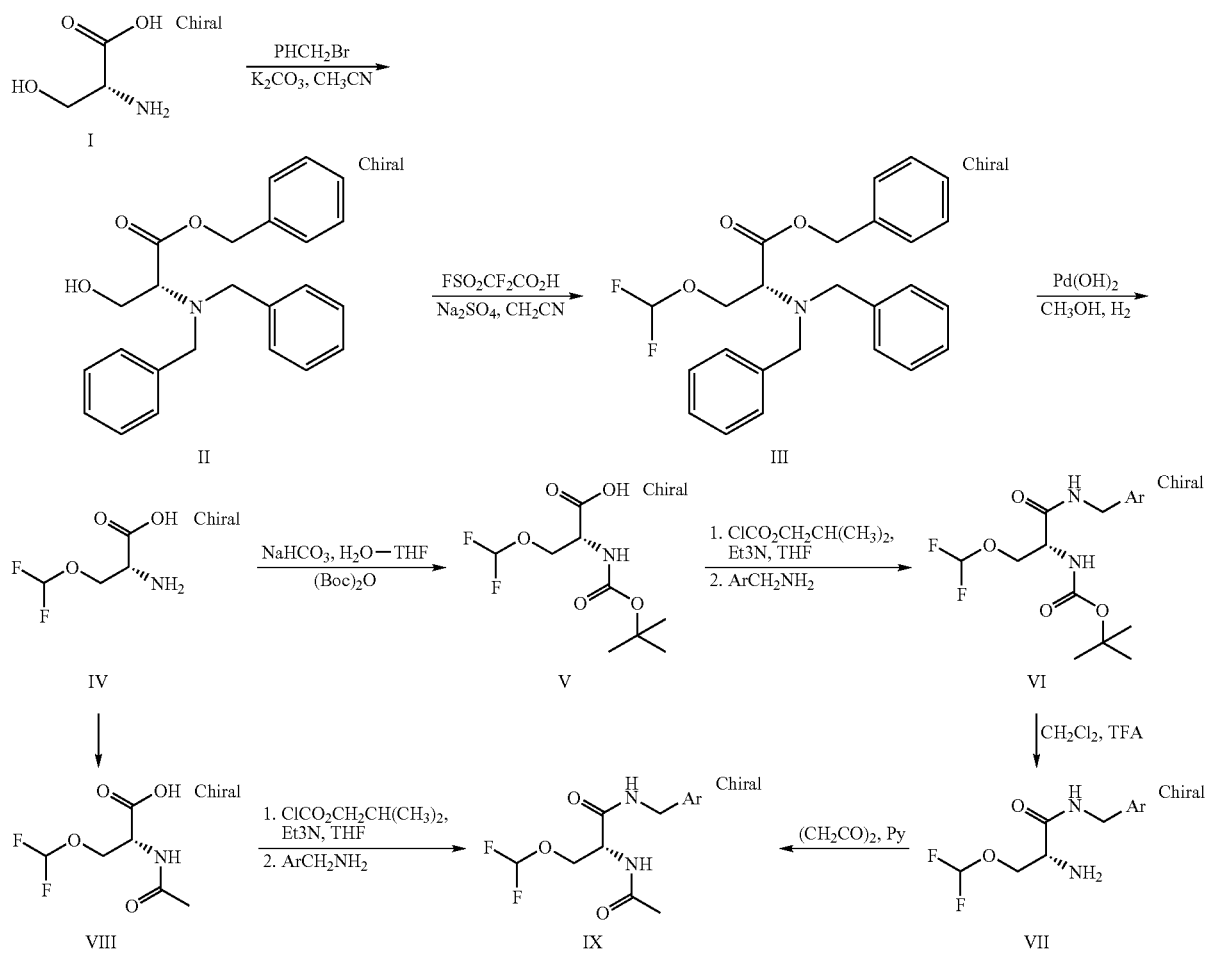

For pharmaceutical use, the compounds of the invention are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intra-arterially, intravenously or intrathecally. Administration can be by means of a pump for periodic or continuous delivery. The compounds of the invention are administered alone, or are combined with a pharmaceutically-acceptable carrier or excipient according to standard pharmaceutical practice. For the oral mode of administration, the compounds of the invention are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530-1533 for further discussion of suppository dosage forms. Analogous gels or creams can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present invention include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present invention include those derived from non-toxic metals such as sodium or potassium, ammonium salts and organoamino salts such as triethylamine salts. Numerous appropriate such salts will be known to those of ordinary skill.

The physician or other health care professional can select the appropriate dose and treatment regimen based on the subject's weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

EXAMPLES

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet). Unless otherwise indicated, in the tables below $^1$H NMR data was obtained at 300 MHz, using CDCl$_3$ as the solvent.

Purification of products were also done using Chem Elut Extraction Columns (Varian, cat #1219-8002), Mega BE-SI (Bond Elut Silica) SPE Columns (Varian, cat # 12256018; 12256026; 12256034), or by flash chromatography in silica-filled glass columns.

Example 1.1

Methyl 2-(dibenzylamino)-3-hydroxypropanoate

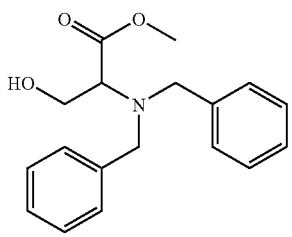

Methyl serine hydrochloride (15 g, 0.096 mol) was stirred with potassium carbonate (66.6 g, 0.482 mol) and benzyl bromide (41.2 g, 0.24 mol) in acetonitrile (240 mL) at room temperature for 24 hours. The reaction mixture was filtered and washed with ethyl acetate. The filtrate was concentrated with silica gel. The product was purified by column chromatography, eluting with 5-20% ethyl acetate in hexanes, to give methyl 2-(dibenzylamino)-3-hydroxypropanoate (27 g, 93.5%) as a pale-yellow sticky oil. $^1$H NMR (300 MHz, CDCl$_3$): δ(ppm) 7.25-7.40 (m, 10H), 3.94 (d, 2H), 3.83 (s, 3H), 3.79 (m, 2H), 3.71 (d, 2H), 3.60 (t, 1H) and 2.62 (t, 1H).

Example 2.1

Methyl 2-dibenzylamino-3-difluoromethoxy-propionate

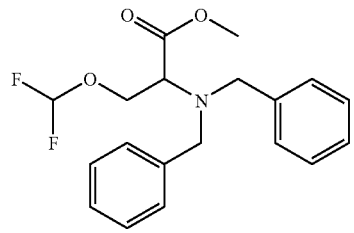

To an acetonitrile solution of methyl 2-(dibenzylamino)-3-hydroxypropanoate (23 g, 76.8 mmol) and sodium sulfate (3.9 g, 27.4 mmol) at 40° C., difluoro(fluorosulfonyl)acetic acid (25 g, 140 mmol) was added dropwise for 1.5 hrs. The reaction mixture was concentrated to dryness and the residue mixed with silica gel in ethyl acetate, then again concentrated to dryness. The product was purified by column chromatography, eluting with 3-4% ethyl acetate in hexanes, to give methyl 2-dibenzylamino-3-difluoromethoxy-propionate (1.3 g, 4.8%) as a colorless oil. $^1$H NMR (300 MHz, CDCl$_3$): δ(ppm) 7.20-7.40 (m, 10H), 6.18 (bt, 1H), 4.05-4.24 (m, 2H), 3.90 (d, 2H), 3.83 (s, 3H) and 3.64-3.71 (m, 3H).

Example 3.1

2-(Dibenzylamino)-3-(difluoromethoxy)propanoic acid

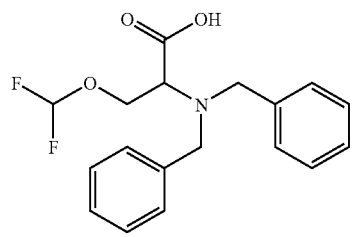

Methyl 2-dibenzylamino-3-difluoromethoxy-propionate (1.2 g, 3.43 mmol) was stirred with 1N LiOH (10.3 mL, 10.3 mmol) in THF (40 mL) at 50° C. for 2 hours and then stirred at room temperature overnight. The reaction mixture was diluted with ethyl acetate and acidified with 1N HCl. The organic layer was dried with sodium sulfate and concentrated with silica gel. The product was purified by column chromatography, eluting with 10-50% ethyl acetate in hexanes, to give 2-(dibenzylamino)-3-(difluoromethoxy)propanoic acid (730 mg, 63.5%) as a white solid. $^1$H NMR (300 MHz, CDCl$_3$): δ(ppm) 7.26-7.42 (m, 10H), 6.29 (bt, 1H), 4.45 (dd, 1H), 4.28 (dd, 1H), 3.94 (q, 4H) and 3.85 (m, 1H).

Example 4.1

2-(Dibenzylamino)-3-(difluoromethoxy)-N-benzyl-propanamide

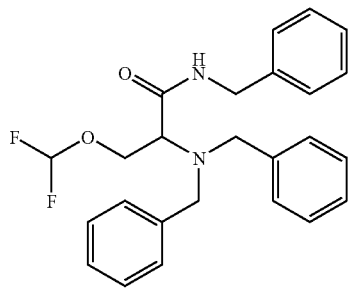

To a solution of 2-(dibenzylamino)-3-(difluoromethoxy) propanoic acid (335.4 mg, 1 mmol) and triethylamine (404.8 mg, 4 mmol) in THF (5 mL) at −5° C., isobutyl chloroformate (143.5 mg, 1.05 mmol) was added dropwise. After 20 minutes, benzylamine hydrochloride (215.4 mg, 1.5 mmol) was added and the reaction mixture allowed to warm up to room temperature. The mixture was then diluted with ethyl acetate and washed with water, 0.5N HCl and Brine. The organic layer was dried over magnesium sulphate, concentrated with silica gel and purified by column chromatography, eluting with 10-20% ethyl acetate in hexanes to give 2-(dibenzylamino)-3-(difluoromethoxy)-N-benzylpropanamide (367 mg, 86.5%) as a white solid. $^1$H NMR (300 MHz, CDCl$_3$): δ(ppm) 7.56 (t, 1H), 7.17-7.34 (m, 15H), 6.35 (wt, 1H), 4.60 (dd, 1H), 4.43 (m, 3H), 3.95 (d, 2H), 3.68 (d, 2H) and 3.67 (m, 1H).

Example 5.1

2-Dibenzylamino-3-difluoromethoxy-N-(4-fluorobenzyl)propionamide

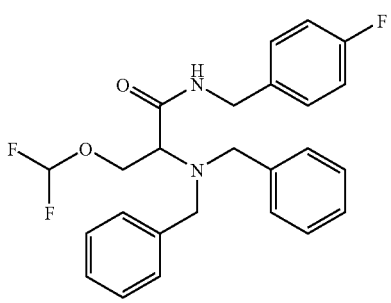

To a solution of 2-(dibenzylamino)-3-(difluoromethoxy) propanoic acid (335.4 mg, 1 mmol) and triethylamine (404.8 mg, 4 mmol) in THF (5 mL) at −5° C., isobutyl chloroformate (143.5 mg, 1.05 mmol) was added dropwise. After 20 minutes, 4-fluorobenzylamine (137.5 mg, 1.1 mmol) was added and the reaction mixture allowed to warm up to room temperature. The mixture then was diluted with ethyl acetate and washed with water, 0.5 N HCl and Brine. The organic layer was dried over magnesium sulphate, concentrated with silica gel and purified by column chromatography, eluting with 10~20% ethyl acetate in hexanes, to give 2-dibenzylamino-3-difluoromethoxy-N-(4-fluorobenzyl)propionamide (395 mg, 89.2%) as a colorless oil. $^1$H NMR (300 MHz, CDCl$_3$): δ(ppm) 7.56 (t, 1H), 6.98-7.32 (m, 14H), 6.35 (wt, 1H), 4.61 (dd, 1H), 4.41 (m, 3H), 3.86 (d, 2H), 3.70 (d, 2H) and 3.68 (m, 1H).

Example 6.1

2-Dibenzylamino-N-(3,4-difluoro-benzyl)-3-difluoromethoxy-propion-amide

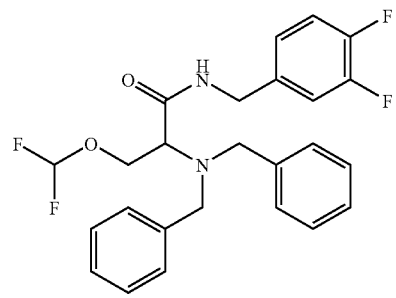

To a solution of 2-(dibenzylamino)-3-(difluoromethoxy) propanoic acid (280 mg, 0.835 mmol) and triethylamine (338 mg, 3.34 mmol) in THF (5 mL) at −5° C., isobutyl chloroformate (119.8 mg, 0.876 mmol) was added dropwise. After 20 minutes, 3,4-difluorobenzylamine (131.3 mg, 0.919 mmol) was added and the reaction mixture allowed to warm up to 0° C. for another hour. The mixture was then diluted with ethyl acetate and washed with water, 0.5 N HCl and Brine. The organic layer was dried over magnesium sulphate, concentrated with silica gel and purified by column chromatography, eluting with 10~20% ethyl acetate in hexanes, to give 2-dibenzylamino-N-(3,4-difluoro-benzyl)-3-difluoromethoxy-propionamide (298 mg, 77.5%) as a colorless oil. $^1$H NMR (300 MHz, CDCl$_3$): δ(ppm) 7.56 (t, 1H), 6.82-7.38 (m, 13H), 6.60 (wt, 1H), 4.58 (dd, 1H), 4.37 (m, 3H), 3.90 (d, 2H), 3.73 (d, 2H) and 3.70 (m, 1H).

Example 7.1

2-Amino-N-benzyl-3-(difluoromethoxy)propanamide

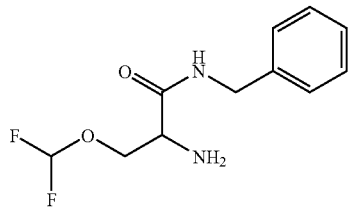

2-(Dibenzylamino)-3-(difluoromethoxy)-N-benzylpropanamide (362 mg, 0.863 mmol) was stirred with 10% Pd(OH)$_2$ (200 mg) in ethanol under H$_2$ overnight. The reaction mixture was filtered and concentrated to give 2-amino-N-benzyl-3-(difluoromethoxy)propanamide (195 mg, 93.6%) as a colorless oil. $^1$H NMR (300 MHz, CDCl$_3$): δ(ppm) 7.83 (t, 1H), 7.25-7.40 (m, 5H), 6.27 (wt, 1H), 4.49 (d, 2H), 4.19 (d, 2H) and 3.68 (m, 1H).

Example 8.1

2-Amino-3-difluoromethoxy-N-(4-fluorobenzyl)propionamide

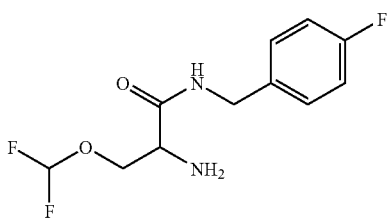

2-Dibenzylamino-3-difluoromethoxy-N-(4-fluorobenzyl)propionamide (390 mg, 0.881 mmol) was stirred with 10% Pd(OH)$_2$ (200 mg) in ethanol under H$_2$ overnight. The reaction mixture was filtered and concentrated to give 2-mino-3-difluoromethoxy-N-(4-fluorobenzyl)propionamide (200 mg, 86.5%) as a colorless oil. $^1$H NMR (300 MHz, DMSO-d6): δ(ppm) 8.88 (t, 1H), 7.31 (dd, 2H), 7.16 (t, 2H), 6.73 (wt, 1H), 4.2 (d, 2H), 4.10 (m, 2H) and 3.89 (m, 1H).

Example 9.1

2-(Acetylamino)-N-benzyl-3-(difluoromethoxy)propanamide

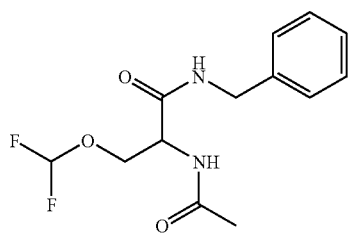

To a solution of 2-amino-N-benzyl-3-(difluoromethoxy)propanamide (195 mg, 0.798 mmol) and triethylamine (322 mg, 3.19 mmol) in THF (5 mL), acetic hydride (98.5 mg, 0.958 mmol) was added. The reaction mixture was stirred at room temperature for an hour, diluted with ethyl acetate and washed with water. The organic layer was concentrated with silica gel and purified by column chromatography, eluting with 50-100% ethyl acetate in hexanes. The product was triturated with diethyl ether to give 2-(acetylamino)-N-benzyl-3-(difluoromethoxy)propanamide (135 mg, 59%) as a white solid, MP: 173.3° C. $^1$H NMR (300 MHz, CDCl$_3$): δ(ppm) 7.25-7.39 (m, 5H), 6.68 (w, 1H), 6.42 (d, 1H), 6.24 (wt, 1H), 4.73 (m, 1H), 4.48 (d, 2H), 4.24 (dd, 1H), 4.01 (dd, 1H) and 2.05 (s, 3H).

Example 10.1

2-(Acetylamino)-3-(difluoromethoxy)-N-(4-fluorobenzyl)propan-amide

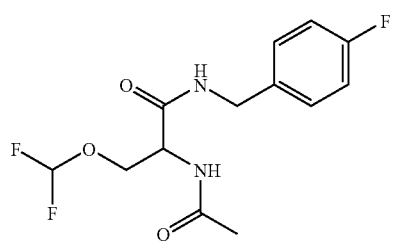

To a solution of 2-amino-3-difluoromethoxy-N-(4-fluorobenzyl)propionamide (200 mg, 0.762 mmol) and triethylamine (293 mg, 2.9 mmol) in THF (5 mL), acetic hydride (93 mg, 0.915 mmol) was added. The reaction mixture was stirred at room temperature for three hours, diluted with ethyl acetate, and washed with water. The organic layer was concentrated with silica gel and purified by column chromatography with 50-100% ethyl acetate in hexanes. The product was triturated with diethyl ether to give 2-(acetylamino)-N-benzyl-3-(difluoromethoxy)propanamide (140 mg, 60.3%) as a white solid, MP: 130.8° C. $^1$H NMR (300 MHz, CDCl$_3$): δ(ppm) 7.24 (dd, 2H), 7.03 (t, 2H), 6.73 (w, 1H), 6.41 (d, 1H), 6.24 (wt, 1H), 4.71 (m, 1H), 4.44 (d, 2H), 4.24 (dd, 1H), 4.01 (dd, 1H) and 2.05 (s, 3H).

Example 11.1

2-(Acetylamino)-N-(3,4-difluorobenzyl)-3-(difluoromethoxy)propan-amide

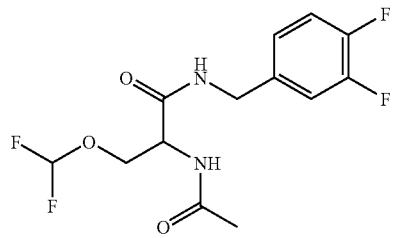

2-dibenzylamino-N-(3,4-difluoro-benzyl)-3-difluoromethoxy-propionamide (298 mg, 0.645 mmol) was stirred with 10% Pd(OH)$_2$ (200 mg) in ethanol under H$_2$ overnight. The reaction mixture was filtered and concentrated. The residue was mixed with triethylamine (254 mg, 2.5 mmol) in dichloromethane (2 mL) and treated with acetic anhydride (85 μL) at room temperature for 2 hours. The reaction mixture was diluted with dichloromethane and washed with water. The organic layer was concentrated with silica gel and purified by column chromatography, eluting with 30-100% ethyl acetate in hexanes. The product was triturated with diethyl ether to give 2-amino-N-(3,4-difluorobenzyl)-3-(difluoromethoxy)propanamide (125 mg, 60%) as a white solid, MP: 146° C. $^1$H NMR (300 MHz, CDCl$_3$): δ(ppm) 6.92-7.16 (m, 4H), 6.47 (d, 1H), 6.25 (wt, 1H), 4.75 (m, 1H), 4.41 (m, 2H), 4.22 (dd, 1H), 4.02 (dd, 1H) and 2.05 (s, 3H).

Example 12.1

Benzyl (2R)-2-(dibenzylamino)-3-hydroxypropanoate

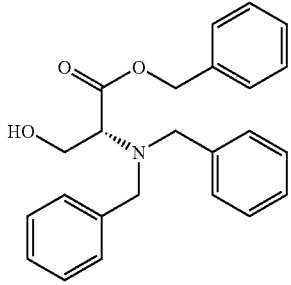

D-serine (10.5 g, 0.1 mol) was stirred with potassium carbonate (69 g, 0.5 mol), benzyl bromide (64.8 g, 0.375 mol) and water (10 mL) in acetonitrile (250 mL) at 55° C. for 24 hours. The reaction mixture was filtered and washed with ethyl acetate. The filtrate was concentrated with silica gel. The product was purified by column chromatography, eluting with 5-20% ethyl acetate in hexanes to give benzyl (2R)-2-(dibenzylamino)-3-hydroxypropanoate (33.36 g, 88%) as a pale-yellow sticky oil. $^1$H NMR (300 MHz, CDCl$_3$): δ(ppm) 7.20-7.44 (m, 15H), 5.27 (q, 2H), 3.91 (d, 2H), 3.80 (m, 2H), 3.67 (d, 2H), 3.63 (m, 1H) and 2.52 (dd, 1H).

Example 13.1

Benzyl (2R)-2-(dibenzylamino)-3-difluoromethoxy-propionate

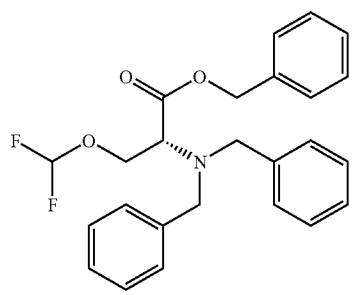

To a mixture of Benzyl (2R)-2-(dibenzylamino)-3-hydroxypropanoate (22.2 g, 59.2 mmol) and sodium sulfate (2.0 g, 14 mmol) in acetonitrile (200 mL) at 40° C., difluoro(fluorosulfonyl)acetic acid (10.5 g, 59.2 mmol) was added dropwise for 1.5 hrs. The reaction mixture was concentrated to dryness. The residue was mixed with ethyl acetate and silica gel, then concentrated again and purified by column chromatography, eluting with 1.5-2.5% ethyl acetate in hexanes to give benzyl (2R) 2-dibenzylamino-3-difluoromethoxy-propionate (3.375 g, 13.4%) as a colorless oil. $^1$H NMR (300 MHz, CDCl$_3$): δ(ppm) 7.20-7.40 (m, 15H), 6.17 (wt, 1H), 5.27 (q, 2H), 4.22 (dd, 1H), 4.10 (dd, 1H), 3.88 (d, 2H), 3.74 (t, 1H) and 3.65 (d, 2H).

Example 14.1

(2R)-2-Amino-3-(difluoromethoxy)propanoic acid

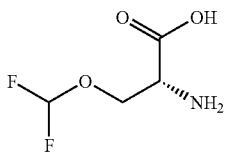

Benzyl (2R) 2-dibenzylamino-3-difluoromethoxy-propionate (3.1 g, 6.28 mmol) was stirred with Pd(OH)$_2$ in methanol under H$_2$ overnight. The reaction mixture was filtered and the filtrate concentrated to dryness, then triturated with diethyl ether to give (2R)-2-amino-3-(difluoromethoxy)propanoic acid (773 mg, 68.4%) as a white solid. $^1$H NMR (300 MHz, MeOD): δ(ppm) 6.49 (wt, 1H), 4.33 (dd, 1H), 4.22 (dd, 1H), and 3.88 (dd, 1H).

Example 15.1

(2R)-2-[(tert-Butoxycarbonyl)amino]-3-(difluoromethoxy)propanoic acid

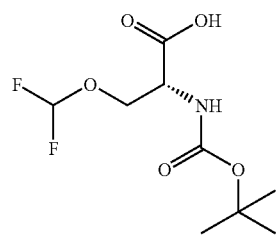

(2R)-2-Amino-3-(difluoromethoxy)propanoic acid (380 mg, 2.45 mmol) was stirred with sodium bicarbonate (411.6 mg. 4.90 mmol) and di-tert-butyl dicarbonate (902 mg, 3.68 mmol) in water (6 mL) and THF (2 mL) at room temperature overnight. The reaction mixture was diluted with water and extracted with ether to remove excess di-tert-butyl dicarbonate. The aqueous layer was acidified with 1N HCl to pH2 and extracted with ethyl acetate, dried over magnesium sulphate and concentrated to give (2R)-2-[(tert-butoxycarbonyl)amino]-3-(difluoromethoxy)propanoic acid (515 mg, 82.3%) as a colorless sticky oil. $^1$H NMR (300 MHz, CDCl$_3$): δ(ppm) 6.23 (wt, 1H), 5.35 (d, 1H), 4.60 (m, 1H), 4.33 (m, 1H), 4.17 (m, 1H) and 1.51 (s, 9H).

Example 16.1 tert-Butyl {(1R)-2-(benzylamino)-1-[(difluoromethoxy)methyl]-2-oxoethyl}carbamate

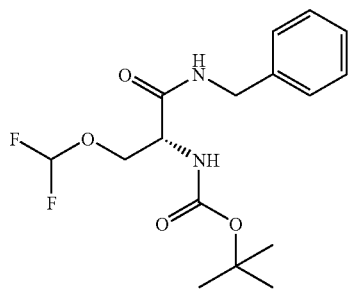

To a solution of (2R)-2-[(tert-butoxycarbonyl)amino]-3-(difluoromethoxy)propanoic acid (510 mg, 2.0 mmol) and triethylamine (607.1 mg, 6 mmol) in THF (10 mL) at −78° C., isobutyl chloroformate (348 mg, 2.55 mmol) was added dropwise. After 30 minutes, benzylamine (321.5 mg, 3.0 mmol) was added and the reaction mixture allowed to warm up to room temperature. The mixture then was diluted with ethyl acetate and washed with water, 0.5N HCl and Brine. The organic layer was dried over magnesium sulphate, concentrated, and triturated with ether-hexanes (1:3) to give tert-butyl {(1R)-2-(benzylamino)-1-[(difluoromethoxy)methyl]-2-oxoethyl}carbamate (345 mg, 50%) as a white solid. $^1$H NMR (300 MHz, CDCl$_3$): δ(ppm) 7.40-7.80 (m, 5H), 6.60 (t, 1H), 6.22 (wt, 1H), 5.25 (w, 1H), 4.32-4.55 (m, 4H), 4.05 (dd, 1H) and 1.48 (s, 9H).

Example 17.1 tert-Butyl {(1R)-1-[(difluoromethoxy)methyl]-2-[(4-fluorobenzyl) amino]-2-oxoethyl}carbamate

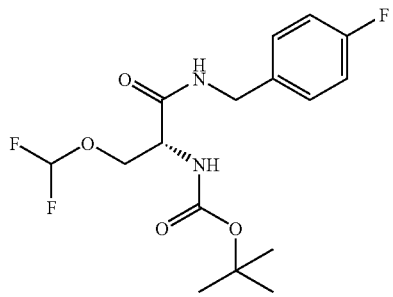

To a solution of (2R)-2-[(tert-butoxycarbonyl)amino]-3-(difluoromethoxy)propanoic acid (780 mg, 3.05 mmol) and triethylamine (924 mg, 9.15 mmol) in THF (15 mL) at −78° C., isobutyl chloroformate (417.7 mg, 3.05 mmol) was added dropwise. After 30 minutes, (4-fluorobenzyl)amine (458 mg, 3.0 mmol) was added and the reaction mixture allowed to warm up to room temperature. The mixture was then diluted with ethyl acetate and washed with water, 0.5N HCl and Brine. The organic layer was dried over magnesium sulphate, concentrated, and triturated with hexanes (1:3) to give tert-butyl {(1R)-1-[(difluoromethoxy)methyl]-2-[(4-fluorobenzyl)amino]-2-oxoethyl}carbamate (870 mg, 78.7%) as a white solid. $^1$H NMR (300 MHz, CDCl$_3$): δ(ppm) 7.23 (dd, 2H), 7.03 (t, 2H), 6.60 (b, 1H), 6.23 (wt, 1H), 5.24 (w, 1H), 4.3-4.51 (m, 4H), 4.02 (dd, 1H) and 1.45 (s, 9H).

Example 18.1 tert-butyl {(1R)-2-[(4-chlorobenzyl)amino]-1-[(difluoromethoxy)methyl]-2-oxoethyl}carbamate

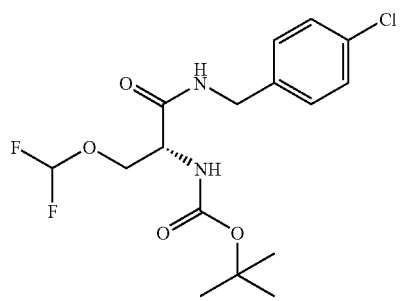

To a solution of (2R)-2-Amino-3-(difluoromethoxy)propanoic acid (500 mg, 1.96 mmol) in THF (15 mL) at −78° C., 4-methylmorpholine (198 mg, 1.96 mmol) followed by isobutyl chloroformate (272 mg, 1.96 mmol) were added dropwise. (4-Chlorobenzyl) amine (332 mg, 2.35 mmol) was then added and the reaction mixture allowed to warm up to room temperature. The mixture was then diluted with ethyl acetate and washed with water and brine. The organic layer was dried over magnesium sulphate, concentrated, and purified by column chromatography to yield tert-butyl {(1R)-2-[(4-chlorobenzyl)amino]-1-[(difluoromethoxy)methyl]-2-oxoethyl}carbamate (652 mg, 88%). $^1$H NMR (300 MHz, CDCl$_3$): δ(ppm) 7.36 (d, 2H), 7.20 (d, 2H), 6.64 (broad, 1H), 6.23 (wt, 1H), 5.24 (broad, 1H), 4.50 (d, 2H), 4.41 (broad, 1H), 4.32 (m, 1H), 4.03 (m, 1H), 1.45 (s, 9H)

In a similar manner the following compounds were synthesized:

| Example | Structure | Name | Yield |
|---|---|---|---|
| 18.2 | 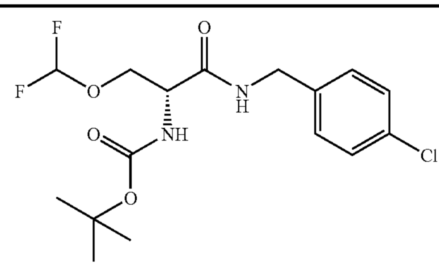 | tert-butyl {(1R)-1-[(difluoromethoxy)methyl]-2-[(3-fluorobenzyl amino]-2-oxoethyl}carbamate | 623 mg, 88% yield |
| NMR | $^1$H NMR (300 MHz, CDCl$_3$): δ(ppm) 7.32 (m, 1H), 7.00 (m, 3H), 6.65 (broad, 1H), 6.24 (wt, 1H), 5.23 (broad, 1H), 4.49 (broad, 2H), 4.43 (broad, 1H), 4.35 (m, 1H), 4.05 (m, 1H), 1.46 (s, 9H) | | |

| Example | Structure | Name | Yield |
|---|---|---|---|
| 18.3 | 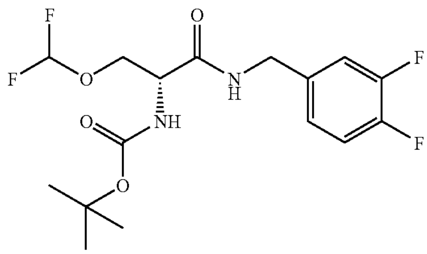 | tert-butyl {(1R)-1-[(difluoromethoxy)methyl]-2-[(3,4-difluorobenzyl)amino]-2-oxoethyl}carbamate | 514 mg, 86% yield |
| NMR | ¹H NMR (300 MHz, CDCl₃): δ(ppm) 7.16 (m, 2H), 7.00 (broad, 1H), 6.67 (broad, 1H), 6.24 (wt, 1H), 5.22 (broad, 1H), 4.46 (broad, 2H), 4.40 (broad, 1H), 4.34 (m, 1H), 4.03 (m, 1H), 1.46 (s, 9H) | | |
| 18.4 | 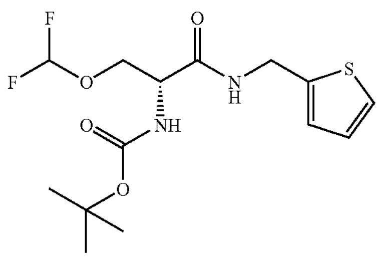 | Tert-butyl {(1R)-1-[(difluoromethoxy)methyl]-2-oxo-2-[(2-thienylmethyl)amino]ethyl}carbamate | 559 mg, 82% yield |
| NMR | ¹H NMR (300 MHz, CDCl₃): δ(ppm) 7.23 (d, 1H), 6.69 (m, 2H), 6.62 (broad, 1H), 6.23 (wt, 1H), 5.22 (broad, 1H), 6.52 (broad, 1H), 4.40 (broad, 1H), 4.32 (m, 1H), 4.02 (m, 1H), 1.45 (s, 9H) | | |
| 18.5 | 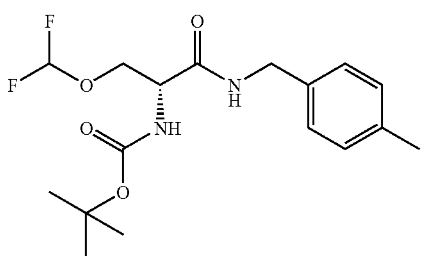 | tert-butyl {(1R)-1-[(difluoromethoxy)methyl]-2-[(4-methylbenzyl)amino]-2-oxoethyl}carbamate | 528 mg, 98% yield |
| NMR | ¹H NMR (300 MHz, CDCl₃): δ(ppm) 7.18 (s, 4H), 6.51 (broad, 1H), 6.24 (wt, 1H), 5.21 (broad, 1H), 4.45 (broad, 2H), 4.40 (broaad, 1H), 4.33 (m, 2H), 4.02 (m, 1H), 2.34 (s, 3H), 1.45 (s, 9H) | | |
| 18.6 | 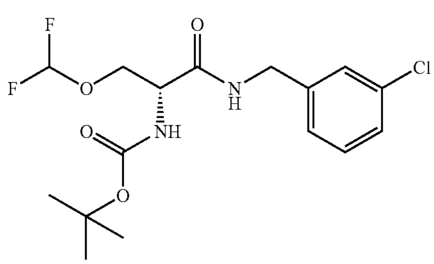 | tert-butyl {(1R)-2-[(3-chlorobenzyl)amino]-1-[(difluoromethoxy)methyl]-2-oxoethyl}carbamate | 354 mg, 95% yield |
| NMR | ¹H NMR (300 MHz, CDCl₃): δ(ppm) 7.26 (m, 3H), 7.15 (m, 1H) <6.65 (broad, 1H), 6.26 (wt, 1H), 5.21 (broad, 1H), 4.48 (broad t, 2H), 4.42 (broad, 1H), 4.35 (m, 1H), 4.04 (m, 1H), 1.46 (s, 9H) | | |

-continued

| Example | Structure | Name | Yield |
|---|---|---|---|
| 18.7 | 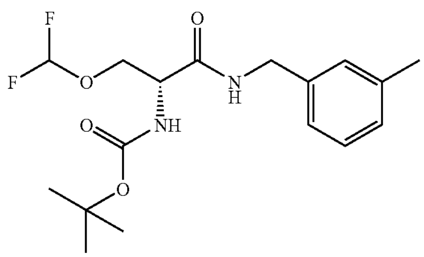 | tert-butyl {(1R)-2-[(3-methylbenzyl)amino]-1-[(difluoromethoxy)methyl]-2-oxoethyl}carbamate | 339 mg, 97% yield |
| NMR | $^1$H NMR (300 MHz, CDCl$_3$): δ(ppm) 7.23 (t, 1H), 7.08 (t, 3H), 6.57 (broad, 1H), 6.23 (wt, 1H), 5.27 (broad, 1H), 4.44 (d, 2H), 4.41 (broad, 1H), 4.32 (m, 1H), 4.03 (m, 1H), 2.34 (s, 3H), 1.45 (s, 9H) | | |
| 18.8 | 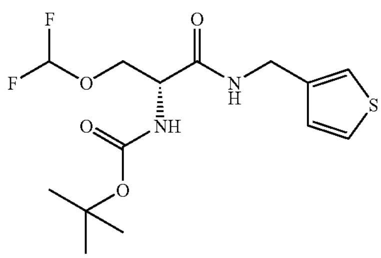 | tert-butyl {(1R)-1-[(difluoromethoxy)methyl]-2-oxo-2-[(3-thienylmethyl)amino]ethyl}carbamate | 330 mg, 96% yield |
| NMR | $^1$H NMR (300 MHz, CDCl$_3$): δ(ppm) 7.31 (m, 1H), 7.15 (s, 1H), 7.01 (d, 1H), 6.56 (broad, 1H), 6.24 (wt, 1H), 5.21 (broad, 1H), 4.49 (d, 1H), 4.40 (broad, 1H), 4.33 (m, 1H), 4.03 (m, 1H), 1.46 (s, 9H) | | |

Example 19.1

(2R)-2-(Acetylamino)-N-benzyl-3-(difluoromethoxy)propanamide (Method A)

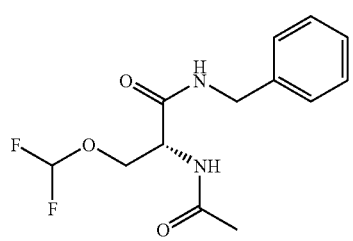

tert-Butyl {(1R)-2-(benzylamino)-1-[(difluoromethoxy)methyl]-2-oxoethyl}carbamate (340 mg, 0.987 mmol) was stirred with trifluoroacetic acid (2.25 mL) and dichloromethane (2.5 mL) in an ice bath for an hour. The reaction mixture was concentrated, stirred with acetic anhydride-pyridine (1:1, 5.8 mL) at room temperature for 30 minutes and then diluted with ethyl acetate, washed with saturated sodium bicarbonate, brine, 0.5N HCl and brine again. The organic layer was dried, concentrated, and triturated with diethyl ether to give (2R)-2-(acetylamino)-N-benzyl-3-(difluoromethoxy)propanamide (230.5 mg, 77.2%) as a white solid. Mp: 186.9° C. $^1$H NMR (300 MHz, DMSO-d6): δ(ppm) 8.60 (t, 1H), 8.30 (d, 1H), 7.28-7.45 (m, 5H), 6.67 (wt, 1H), 4.58 (m, 1H), 4.40 (d, 2H), 3.98 (d, 2H) and 1.88 (s, 3H).

Example 20.1

(2R)-2-(Acetylamino)-3-(difluoromethoxy)-N-(4-fluorobenzyl) propanamide

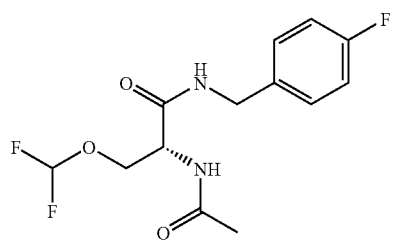

tert-Butyl {(1R)-1-[(difluoromethoxy)methyl]-2-[(4-fluorobenzyl)amino]-2-oxoethyl}carbamate (400 mg, 1.1 mmol) was stirred with trifluoroacetic acid (1.5 mL) and dichloromethane (2.5 mL) in an ice bath for an hour. The reaction mixture was concentrated, mixed with acetic anhydride-pyridine (1:1.6 mL) at room temperature for 30 minutes and then diluted with ethyl acetate, washed with saturated sodium bicarbonate, brine, 0.5N HCl and brine again. The organic layer was dried, concentrated, and triturated with diethyl ether to give (2R)-2-(acetylamino)-3-(difluoromethoxy)-N-(4-fluorobenzyl)propanamide (220 mg, 65.7%) as a white solid. Mp: 162.7° C. $^1$H NMR (300 MHz, CDCl$_3$): δ(ppm)

7.24 (dd, 2H), 7.03 (t, 2H), 6.78 (w, 1H), 6.35 (d, 1H), 6.24 (wt, 1H), 4.71 (m, 1H), 4.44 (d, 2H), 4.24 (dd, 1H), 4.01 (dd, 1H) and 2.05 (s, 3H).

Example 21.1

(2R)-2-(Acetylamino)-3-(difluoromethoxy)propanoic acid

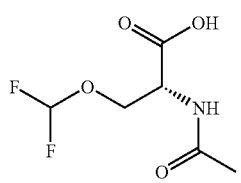

(2R)-2-Amino-3-(difluoromethoxy)propanoic acid (680 mg, 4.39 mmol) was mixed with sodium bicarbonate (738 mg. 8.78 mmol) and acetic anhydride (491 mg, 4.82 mmol) in water (10 mL) and dioxane (10 mL) at 0° C. to room temperature overnight. The reaction mixture was acidified with 1N HCl to pH2, concentrated and extracted with ethyl acetate, and concentrated again to give (2R)-2-(Acetylamino)-3-(difluoromethoxy)propanoic acid (580 mg, 82.3%) as a colorless sticky oil. $^1$H NMR (300 MHz, CDCl$_3$): δ(ppm) 6.40 (d, 1H), 6.24 (wt, 1H), 4.88 (m, 1H), 4.36 (dd, 1H), 4.22 (dd, 1H), 2.12 (s, 3H).

Example 22.1

(2R)-2-(Acetylamino)-N-benzyl-3-(difluoromethoxy)propanamide (method B)

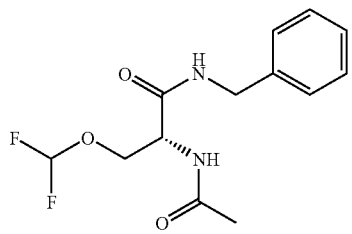

To a solution of (2R)-2-[(tert-butoxycarbonyl)amino]-3-(difluoromethoxy)propanoic acid (197 mg, 1.0 mmol) and triethylamine (303 mg, 3 mmol) in THF (10 mL) at –78° C., isobutyl chloroformate (174 mg, 1.28 mmol) was added dropwise. After 30 minutes, benzylamine (161 mg, 1.5 mmol) was added and the reaction mixture allowed to warm up to room temperature. The mixture then was diluted with ethyl acetate and washed with water, 0.5N HCl and Brine. The organic layer was dried over magnesium sulphate, concentrated, and triturated with ether-hexanes (1:3) to give (2R)-2-(acetylamino)-N-benzyl-3-(difluoromethoxy)propanamide (48 mg, 16.7%) as a white solid. $^1$H NMR (300 MHz, CDCl$_3$): δ(ppm) 7.25-7.39 (m, 5H), 6.68 (w, 1H), 6.42 (d, 1H), 6.24 (wt, 1H), 4.73 (m, 1H), 4.48 (d, 2H), 4.24 (dd, 1H), 4.01 (dd, 1H) and 2.05 (s, 3H).

Example 23.1

(2R)—N-benzyl-3-(difluoromethoxy)-2-[(methylsulfonyl)amino]propanamide

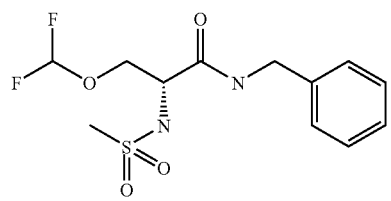

A solution of (2R)-2-amino-N-benzyl-3-(difluoromethoxy)propanamide (113 mg, 0.46 mmol) in ethyl acetate was cooled in an ice bath. To the cooled solution was added triethylamine (139 mg, 1.38 mmol) followed by methanesulfonylchloride (63 mg, 0.55 mmol). The reaction mixture was stirred for 15 minutes and then quenched with water, extracted with ethyl acetate and washed with brine. The organic layer was dried, concentrated and triturated with diethyl ether to give the product (33 mg, 22%) as a white solid. $^1$H NMR (300 MHz, CDCl$_3$): δ(ppm) 7.31 (m, 5H), 6.73 (br, 1H), 6.24 (t, 1H), 5.21 (d, 1H), 4.48 (d, 2H), 4.21 (m, 3H), 3.01 (s, 3H)

In a similar manner the following compound was prepared:

| Example | Structure | Name | Yield |
|---------|-----------|------|-------|
| 23.2 | 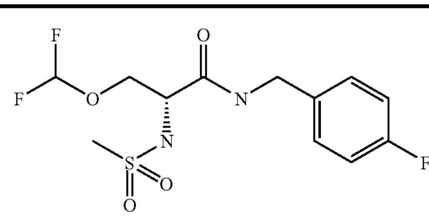 | (2R)-3-(difluoromethoxy)-N-(4-fluorobenzyl)-2-[(methylsulfonyl)amino]propanamide | White solid, 96 mg, 30% |
| NMR | $^1$H NMR (300 MHz, CDCl$_3$): δ(ppm) 7.23 (m, 2H), 7.03 (dd, 2H), 6.76 (br, 1H), 6.22 (t, 1H), 5.16 (dd, 1H), 4.45 (dd, 1H), 4.12 (m, 3H), 2.99 (s, 3H) | | |

Example 24.1

(2R)-2-(acetylamino)-N-(4-chlorobenzyl)-3-(difluoromethoxy) propanamide

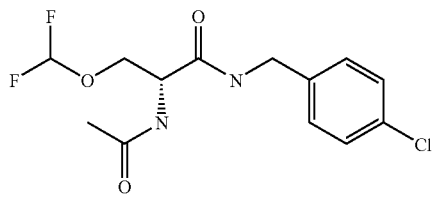

A solution of tert-butyl {(1R)-2-[(4-chlorobenzyl)amino]-1-[(difluoromethoxy)methyl]-2-oxoethyl}carbamate (652 mg, 1.72 mmol) in dichloromethane (7 mL) was cooled in an ice-water bath and trifluoroacetic acid (7 mL) was added and stirred for 30 minutes. The mixture was concentrated and diluted with water and basified, extracting with ethyl acetate. The organic extracts were washed with brine, dried over magnesium sulphate and concentrated to yield the product (444 mg, 92%), which was dissolved in ethyl acetate and cooled in an ice bath. To the cooled solution was added triethylamine (242 mg, 2.4 mmol) followed by acetyl chloride (118 mg, 1.2 mmol). The reaction mixture was stirred for 15 minutes and then quenched with water, extracted with ethyl acetate and washed with brine. The organic layer was dried, concentrated and triturated with diethyl ether to give (2R)-2-(acetylamino)-N-(4-chlorobenzyl)-3-(difluoromethoxy)propanamide (446 mg, 87%). $^1$H NMR (300 MHz, CDCl$_3$): δ(ppm) δ(ppm) 8.64 (t, 1H), 8.26 (d, 1H), 7.41 (d, 2H), 7.22 (d, 2H), 6.42 (t, 1H), 4.58 (q, 1H), 4.27 (d, 2H), 3.98 (d, 2H), 1.88 (s, 3H).

In a similar manner the following compounds were prepared:

| Example | Structure | Name | Yield |
|---|---|---|---|
| 24.2 | 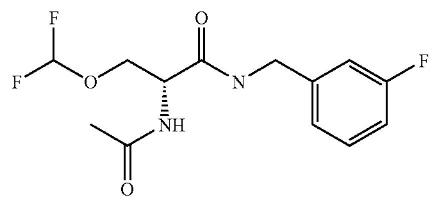 | (2R)-2-(acetylamino)-3-(difluoromethoxy)-N-(3-fluorobenzyl)propanamide | White solid, 422 mg, 86% |
| NMR | $^1$H NMR (300 MHz, CDCl$_3$): 8.64 (t, 1H), 8.27 (d, 1H), 7.34 (m, 1H), 7.03 (m, 3H), 6.66 (wt, 1H), 4.56 (m, 1H), 4.32 (d, 2H), 4.00 (d, 2H), 1.89 (s, 3H) | | |
| 24.3 | 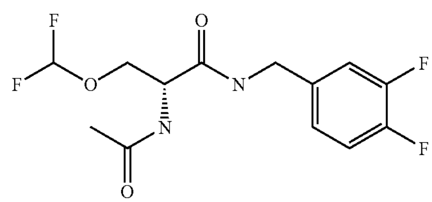 | (2R)-2-(acetylamino)-N-(3,4-difluorobenzyl)-3-(difluoromethoxy)propanamide | White solid, 320 mg, 76% |
| NMR | $^1$H NMR (300 MHz, DMSO): δ(ppm) 8.64 (t, 1H), 8.27 (d, 1H), 7.32 (m, 2H), 7.08 (br, 1H), 6.66 (t, 1H), 4.56 (q, 1H), 4.27 (d, 2H), 3.99 (d, 2H), 1.89 (s, 3H) | | |
| 24.4 | 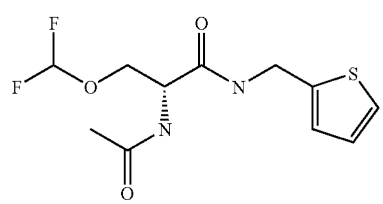 | (2R)-2-(acetylamino)-3-(difluoromethoxy)-N-(2-thienylmethyl)propanamide | White solid, 376 mg, 92% |
| NMR | $^1$H NMR (300 MHz, DMSO): δ(ppm) 8.69 (t, 1H), 8.24 (d, 1H), 7.38 (m, 1H), 6.94 (m, 2H), 6.64 (t, 1H), 4.55 (q, 1H), 4.43 (d, 2H), 3.96 (m, 2H), 1.87 (s, 3H) | | |
| 24.5 | 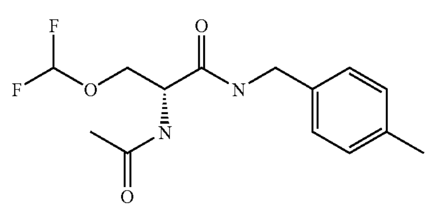 | (2R)-2-(acetylamino)-3-(difluoromethoxy)-N-(4-methylbenzyl)propanamide | White solid, 337 mg, 83% |
| NMR | $^1$H NMR (300 MHz, DMS): δ(ppm) 8.56 (t, 1H), 8.24 (d, 1H), 7.11 (m, 4H), 6.66 (t, 1H), 4.57 (q, 1H), 4.23 (d, 2H), 3.97 (d, 2H), 2.26 (s, 3H), 1.88 (s, 3H) | | |

| Example | Structure | Name | Yield |
|---|---|---|---|
| 24.6 | 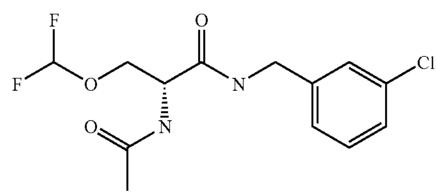 | (2R)-2-(acetylamino)-N-(3-chlorobenzyl)-3-(difluoro-methoxy) propanamde | White solid, 240 mg, 80% |
| NMR | $^1$H NMR (300 MHz, DMSO): δ(ppm) 8.64 (t, 1H), 8.27 (dd, 1H), 7.31 (m, 3H), 7.2 (dd, 1H), 6.66 (t, 1H), 4.57 (q, 1H), 4.29 (dd, 2H), 4.02 (dd, 2H), 1.89 (s, 3H) | | |
| 24.7 | 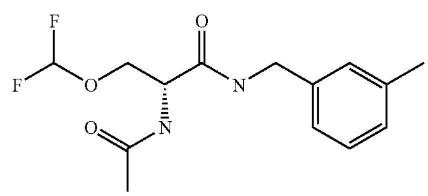 | (2R)-2-(acetylamino)-3-(difluoro-methoxy)-N-(3-methylbenzyl) propanamide | White solid, 212 mg, 74% |
| NMR | $^1$H NMR (300 MHz, DMSO): δ(ppm) 8.56 (t, 1H), 8.24 (d, 1H), 7.18 (t, 1H), 7.03 (m, 3H), 6.66 (t, 1H), 4.58 (q, 1H), 4.25 (d, 2H), 3.99 (d, 2H), 2.27 (s, 3H), 1.88 (s, 3H) | | |
| 24.8 | 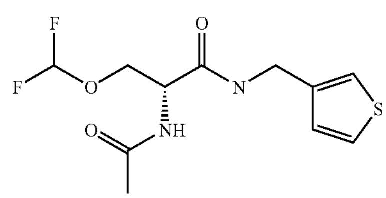 | (2R)-2-(acetylamino)-3-(difluoro-methoxy)-N-(3-thienylmethyl) propanamide | White solid, 195 mg, 78% |
| NMR | $^1$H NMR (300 MHz, DMSO): δ(ppm) 8.55 (t, 1H), 8.23 (d, 1H), 7.46 (dd, 1H), 7.24 (d, 1), 6.99 (d, 1H), 6.66 (t, 1H), 4.57 (q, 1H), 4.27 (d, 2H), 3.97 (d, 2H), 1.88 (s, 3H) | | |

Example 25.1

2-Acetylamino-N-benzyl-3-difluoromethoxy-propionamide

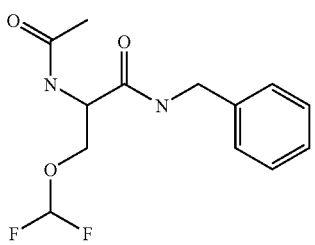

2-Amino-N-benzyl-3-difluoromethoxy-propionamide (195 mg, 0.80) was mixed with triethylamine (322 mg, 3.19 mmol) in THF (5 mL). Acetic anhydride (98.5 mg, 0.96 mmol) was then added and the reaction mixture stirred for 1 hour. The mixture was then diluted with ethyl acetate and washed with water. The organic layer was dried and concentrated. The residue was purified by column chromatography using hexanes:ethyl acetate (50:50 to 0:100). The isolated product was triturated with diethyl ether to give 2-acetylamino-N-benzyl-3-difluoromethoxy-propionamide (135 mg, 59%) as a white solid.

$^1$H NMR (300 MHz, CDCl$_3$): δ(ppm) 7.33 (m, 5H), 6.68 (br, 1H), 6.37 (br, 1H), 6.24 (t, 1H), 4.72 (q, 1H), 4.87 (d, 2H), 4.23 (dd, 1H), 4.01 (dd, 1H), 2.05 (s, 3H).

In a similar manner the following compounds were prepared:

| Example | Structure | Name | Yield |
|---|---|---|---|
| 25.2 | 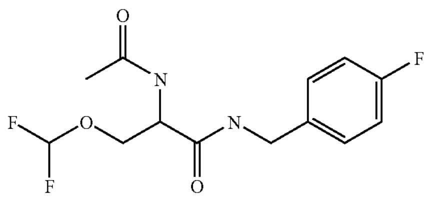 | 2-Acetylamino-3-difluoromethoxy-N-(4-fluoro-benzyl)-propionamide | White solid, 140 mg, 60% |
| NMR | $^1$H NMR (300 MHz, CDCl$_3$): δ(ppm) 7.25 (m, 2H), 7.03 (t, 2H), 6.73 (br, 1H), 6.39 (br, 1H), 6.24 (t, 1H), 4.71 (q, 1H), 4.43 (dd, 2H), 4.25 (dd, 1H), 4.02 (dd, 1H), 2.05 (s, 3H) | | |
| 25.3 | 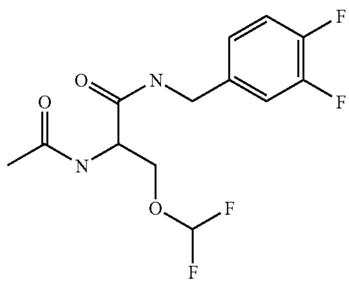 | 2-Acetylamino-N-(3,4-difluoro-benzyl)-3-difluoromethoxy-propionamide | White solid, 125 mg |
| NMR | $^1$H NMR (300 MHz, CDCl$_3$): δ(ppm) 7.11 (m, 4H), 6.5 (br, 1H), 6.24 (t, 1H), 4.75 (q, 1H), 4.42 (dd, 2H), 4.22 (dd, 1H), 3.49 (dd, 1H), 2.05 (s, 3H) | | |

Example 26.1

Maximal Electroshock Assay (Mouse)

Male, CD-1 mice (20-30 g body weight) were orally pretreated with test compound or vehicle control, and either at 1 h or 4 h post dose a maximal electroshock (45 mA amplitude, 0.2 s duration, 60 Hz) was applied by corneal electrodes. Protection was defined by the absence of a tonic extensor seizure in the animal within 20 s of application of the electrical stimulus, which typically occurred in all vehicle pretreated animals. Animals received only one electroshock and so separate animals were used for the 1 h and 4 h timepoints. All drugs were administered in multiple doses. At each dose level the proportion of animals not displaying a tonic extensor seizure was measured and an ED50, i.e effective dose to produce a blockade of tonic seizure in 50% of the animals, was calculated. A ratio of the ED50 obtained at 4 h compared to 1h was determined.

Example 26.2

Maximal Electroshock Assay (Rat)

Male, Sprague-Dawley rats (approx. 100 g body weight) were prescreened for tonic seizure susceptibility prior to drug testing. Only animals which demonstrated a tonic seizure to a maximal electroshock (150 mA amplitude, 0.2 s duration, 60 Hz), 24 h previously were orally pretreated with test compound or vehicle control, and either at 0.5 h or 4 h post dose a maximal electroshock (150 mA amplitude, 0.2 s duration, 60 Hz) was applied by corneal electrodes. Protection was defined by the absence of a tonic extensor seizure in the animal within 20 s of application of the electrical stimulus, which typically occurred in all vehicle pretreated animals.

| | MES oral ED50 1 h | MES oral ED50 4 h | Ratio ED50 4 h vs. 1 h |
|---|---|---|---|
| Lacosamide | 5.3 (3.8-7.5) mg/kg | 32 mg/kg | 6.0 |
| Compound 3 | 5.7 (4.3-7.7) mg/kg | 20.0 (13.2-30.5) mg/kg | 3.5 |
| Compound 4 | 9.8 (6.2-15.5) mg/kg | 9.8 (7.9-12.2) mg/kg | 1.0 |
| Compound 20 | 8.7 (7.8-9.7) mg/kg | 17.9 (12.5-25.6) mg/kg | 2.1 |

Compounds 3, 4, and 20 each had a duration of action longer than Lacosamide, as indicated by similar potency at 1 h and 4 h pretreatment timepoints. While there was an approximate 6-fold shift in ED50 for 1 vs. 4h for Lacosamide, for compounds 3, 4, and 20 this shift was in the range 1 to 3.5 fold.

Animals received only one electroshock on the drug test day and so separate animals were used for the 0.5 h and 4 h timepoints. All drugs were administered in multiple doses. At each dose level the proportion of animals not displaying a tonic extensor seizure was measured and an ED50, i.e effective dose to produce a blockade of tonic seizure in 50% of the animals, was calculated. A ratio of the ED50 obtained at 4 h compared to 0.5 h was determined.

|  | MES oral ED50 0.5 h | MES oral ED50 4 h | Ratio ED50 4 h vs. 0.5 h |
|---|---|---|---|
| Lacosamide | 1.8 (1.6-1.9) mg/kg | 8.3 (8.1-8.4) mg/kg | 4.6 |
| Compound 3 | 3.0 (2.9-3.1) mg/kg | 4.2 (2.6-6.8) mg/kg | 1.4 |
| Compound 4 | 3.3 (2.1-5.2) mg/kg | 3.4 mg/kg | 1.0 |
| Compound 20 | 1.7 (1.6-1.7) mg/kg | 2.0 (0.7-5.3) mg/kg | 1.2 |

Compounds 3, 4 and 20 each had a duration of action longer than Lacosamide, as indicated by similar potency at 0.5 h and 4 h pretreatment timepoints. While there was an approximately 5-fold shift in ED50 for 0.5 vs. 4 h for Lacosamide, for compounds 3, 4, and 20 this shift was 1 to 1.4 fold.

Example 27.1

Persistent Inflammatory Pain (Formalin Model)

The formalin test is a chemically-induced tonic pain model in which injection of formalin into a hind paw elicits a biphasic nociceptive behavior. The second phase of formalin response is predominantly due to a central sensitization phenomenon. Most clinically used drugs against neuropathic pain are active on this second phase of formalin response. Formalin test is accepted as a valid model of persistent clinical pain.

The test was done by pretreating the rats with the test compound and 30 min later (pretreatment time), 50 μl of 2.5% formalin was injected into the right hind paw of the animal. The number of paw licking and flinching episodes were scored for 60 min post-formalin injection.

The compounds were administered either intraperitoneally (30 mg/kg) or orally (60 mg/kg). The compounds significantly inhibited the second phase of the formalin response.

Example 27.2

The effect of the compounds on the two phases of formalin test at 30 mg/kg, i.p.

|  | % Inhibition | |
|---|---|---|
| Compound | Phase I | Phase II |
| Compound 3 | 87.9 ± 12.1*** | 90.2 ± 6.5*** |
| Compound 4 | 94.7 ± 5.3*** | 81.6 ± 10.0*** |
| Compound 20 | 75.27 ± 9.3*** | 82.34 ± 9.7*** |

***$P < 0.001$

The effect of the compounds on the two phases of formalin test at 60 mg/kg, p.o.

|  | % Inhibition | |
|---|---|---|
| Compound | Phase I | Phase II |
| Compound 3 | 21.4 ± 10.2 | 46.1 ± 8.7** |
| Compound 4 | 7.6 ± 6.7 | 41.9 ± 9.0** |
| Compound 20 | 9.6 ± 8.1 | 57.6 ± 7.0*** |

-continued

|  | % Inhibition | |
|---|---|---|
| Compound | Phase I | Phase II |

**$P < 0.01$;
***$P < 0.001$

Example 28.1

Chronic Neuropathic Pain Model (Spared Nerve Injury or SNI Model)

The compounds were tested for their efficacy in reducing mechanical allodynia and cold allodynia in the spared nerve injury (SNI) model of chronic neuropathic pain. In this model, the left sciatic nerve of the rat is exposed under anesthesia. Two of the branches of the sciatic nerve viz. the common peroneal and tibial nerve are ligated and sectioned. The third branch (sural nerve) is left intact. The animals were allowed a post-operative recovery period of 7 days before they were subjected to any test.

Mechanical Allodynia

The presence of mechanical allodynia was assessed using the Dynamic Plantar Aesthesiometer (Ugo Basile, Italy) which is a modified version of the Von Frey Hair test. In this, a test filament is positioned below the animal's hind paw and the unit is activated which causes the filament to move up and touch the plantar surface of the hind paw. Increasing force is applied to the paw via the filament. When the animal withdraws its paw, the unit is inactivated automatically and the threshold force required to elicit the paw withdrawal is displayed. The cut-off force is set at 50 g. The tests were done on both the non-injured (control) and the injured (SNI) paw. Pilot studies showed the presence of mechanical allodynia 7 days after the surgery and lasted up to 4 weeks (end of the test period).

Testing of compounds was done after 21 days post-operatively. After initial basal readings were taken, the test compound or the vehicle was administered (10 ml/kg) either intraperitoneally (30 mg/kg) or orally (60 mg/kg). The readings were taken again 30, 60 and 180 min after the compound/vehicle administration. Mechanical allodynia in neuropathic rats was significantly inhibited by the compounds up to 180 min after the intraperitoneal administration as evidenced by the increase in the withdrawal threshold.

Example 28.2

The effect of the compounds on mechanical allodynia in SNI rats at 30 mg/kg, i.p. Values indicate the withdrawal threshold in g.

The effect of the compounds on mechanical allodynia in SNI rats at 60 mg/kg, p.o. Values indicate the withdrawal threshold in g.

|  | Pre-Admin. | Post Admin | | |
|---|---|---|---|---|
| Compound | 0 min | 30 min | 60 min | 180 min |
| Compound 3 | 7.5 ± 1.4 | 22.5 ± 2.1*** | 20.0 ± 2.1*** | 14.1 ± 1.6*** |
| Compound 4 | 6.7 ± 0.7 | 16.7 ± 1.4*** | 15.0 ± 0.8*** | 13.2 ± 1.0*** |
| Compound 20 | 12.4 ± 1.3 | 24.9 ± 4.4*** | 25.3 ± 3.2*** | 26.3 ± 2.5*** |

***P < 0.001 (vs Pre-Admin. Values)

|  | Pre-Admin. | Post Admin | | |
|---|---|---|---|---|
| Compound | 0 min | 30 min | 60 min | 180 min |
| Compound 3 | 9.7 ± 2.5 | 19.4 ± 2.3*** | 20.6 ± 3.1*** | 10.8 ± 1.8 |
| Compound 4 | 7.5 ± 0.5 | 15.4 ± 1.1*** | 16.2 ± 1.7*** | 7.9 ± 0.6 |
| Compound 20 | 7.5 ± 0.5 | 19.3 ± 1.8*** | 20.3 ± 1.6*** | 14.7 ± 0.9*** |

***P < 0.001 (vs Pre-Admin. Values)

Cold Allodynia

Cold allodynia was assessed by using the acetone test. In this model, 25 µl of acetone is sprayed on to the plantar surface of the hind paw. Evaporation of acetone causes cooling of the skin. The cold stimulus sets up nociceptive responses from the injured paw as evidenced by paw lifting, paw licking and grooming. The duration of the nociceptive responses is noted. Similar stimulus to the uninjured (control) paw usually does not elicit nociceptive responses.

Testing of compounds was done after 21 days post-operatively. After initial basal readings were taken, the test compound or the vehicle was administered (10 ml/kg) either intraperitoneally (30 mg/kg) or orally (60 mg/kg). The readings were taken 30 min after the administration. Cold allodynia in neuropathic rats was significantly inhibited by the compounds as evidenced by the reduced nociceptive duration in these animals.

Example 28.3

The effect of the compounds on cold allodynia in SNI rats at 30 mg/kg, i.p. Values indicate the duration (s) of nociceptive response

|  | Pre-Admin. | Post Admin |
|---|---|---|
| Compound | 0 min | 30 min |
| Compound 3 | 45.8 ± 9.4 | 4.3 ± 1.6*** |
| Compound 4 | 48.2 ± 10.1 | 3.1 ± 2.1*** |
| Compound 20 | 45.6 ± 6.9 | 3.4 ± 2.1*** |

***P < 0.001 (vs Pre-Admin. Values)

The effect of the compounds on cold allodynia in SNI rats at 60 mg/kg, p.o. Values indicate the duration (s) of nociceptive response.

|  | Pre-Admin. | Post Admin |
|---|---|---|
| Compound | 0 min | 30 min |
| Compound 3 | 70.7 ± 18.9 | 17.2 ± 6.2*** |
| Compound 4 | 56.2 ± 8.4 | 21.9 ± 6.4*** |
| Compound 20 | 33.3 ± 4.3 | 16.6 ± 6.3*** |

***P < 0.001 (vs Pre-Admin. Values)

Example 29.1

Chronic Inflammatory Pain Model (Freund's Complete Adjuvant or FCA Model)

Administration of FCA to the hind paw of an animal induces the formation of a localized edema and has been widely used as a model of chronic inflammatory pain. 100 µl of FCA is injected subcutaneously into the dorsal aspect of the left hind paw of the rats. The edema appears within 2 h reaches a peak by 6 h and lasts for about 7 days. The effects of compounds on mechanical allodynia and paw volume were studied 2 days after FCA administration.

Mechanical Allodynia

The effect of the compounds in alleviating mechanical allodynia was assessed in the FCA-treated rats using the modified Randall-Selitto method (Analgesy-Meter, Ugo Basile, Italy). The animal's paw is placed on a small plinth under a cone-shaped pusher. Increasing force is applied to the paw by depressing a pedal until vocalization or withdrawal of the paw occurs. The minimum force required to elicit this vocalization/withdrawal is the paw pressure threshold. The cut-off was set at 150 g.

After the initial basal (control) readings were taken, the test compound (60 mg/kg)/vehicle was administered orally in a volume of 10 ml/kg. The paw pressure thresholds were measured 30, 60 and 180 min post administration. A significant inhibition of mechanical allodynia was seen at 30 min by all compounds tested. Some of the compounds were effective even at 60 and 180 min post administration.

Example 29.2

The effect of the compounds on mechanical allodynia in FCA-treated rats at 60 mg/kg, p.o. Values indicate the paw withdrawal threshold (g).

|  | Pre-Admin. | Post Admin | | |
|---|---|---|---|---|
| Compound | 0 min | 30 min | 60 min | 180 min |
| Compound 3 | 32.8 ± 6.5 | 57.8 ± 4.9** | 46.7 ± 3.8 | 37.8 ± 5.4 |
| Compound 4 | 33.9 ± 4.2 | 58.3 ± 4.8** | 49.4 ± 6.4** | 51.1 ± 8.9** |
| Compound 20 | 23.3 ± 2.1 | 67.1 ± 9.9*** | 60.4 ± 5.8*** | 64.2 ± 5.6*** |

**P < 0.01,
***P < 0.001 (vs Pre-Admin. Values)

Paw Edema/Volume

The edema/volume of the paw is a measure of inflammation induced by FCA. This was measured by using a plethysmometer (Ugo Basile, Italy). In this, the paw of the rat is immersed in a reservoir of water and the volume of water displaced indicates the paw volume.

After the initial basal (control) readings were taken, the test compound (60 mg/kg)/vehicle was administered orally in a volume of 10 ml/kg. The paw volume was measured 30 and 60 min post administration. None of the compounds tested significantly altered the paw volume.

Example 29.3

The effect of the compounds on paw volume (ml) of FCA-treated rats at 60 mg/kg, p.o.

|  | Pre-Admin. | Post Admin | |
|---|---|---|---|
| Compound | 0 min | 30 min | 60 min |
| Compound 3 | 2.3 ± 0.0 | 2.3 ± 0.1 | 2.3 ± .01 |
| Compound 4 | 2.01 ± 0.0 | 2.08 ± 0.0 | 2.11 ± 0.0 |
| Compound 20 | 2.3 ± 0.1 | 2.3 ± 0.1 | 2.3 ± 0.1 |

Conclusion

Compounds of the invention were effective in significantly reducing the nociceptive responses during the second phase of formalin test. They were effective in reducing the mechanical allodynia in both the chronic models of pain vs. neuropathic and inflammatory pain. Cold allodynia in the neuropathic rats was also significantly reduced by these compounds.

We claim:
1. A compound of Formula I or a salt thereof:

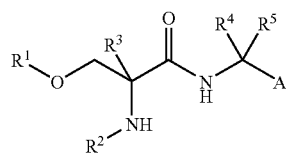

Formula I wherein:
A is selected from the group consisting of aryl and heteroaryl, optionally substituted with one or more independently-selected groups $R^8$;
$R^1$ is a haloalkyl group;
$R^2$ is selected from the group consisting of $C(O)R^6$, $C(O)OR^6$, $SO_2R^6$ and $C(O)NR^6R^7$;
$R^3$, $R^4$ and $R^5$ are independently selected from the group consisting of H and alkyl;

$R^6$ and $R^7$ are independently selected from the group consisting of H and alkyl; and
$R^8$ is selected from the group consisting of OH, CN, halo, alkyl, alkoxy, haloalkyl, haloalkoxy, $C(O)R^6$, $C(O)OR^6$, $SO_2R^6$ and $C(O)NR^6R^7$.

2. A compound according to claim 1, wherein A is a phenyl group.

3. A compound according to claim 2, wherein $R^8$ is halo.

4. A compound according to claim 3, wherein $R^2$ is $C(O)R^6$.

5. A compound selected from the group consisting of:
2-Amino-N-benzyl-3-(difluoromethoxy)propanamide,
2-Amino-3-difluoromethoxy-N-(4-fluorobenzyl)propionamide,
2-(Acetylamino)-N-benzyl-3-(difluoro-methoxy)propanamide,
2-(Acetylamino)-3-(difluoromethoxy)-N-(4-fluoro-benzyl)propanamide,
2-(Acetylamino)-N-(3,4-difluorobenzyl)-3-(difluoromethoxy)propanamide,
tert-Butyl {(1R)-2-(benzylamino)-1-[(difluoromethoxy)methyl]-2-oxoethyl}carbamate,
tert-Butyl {(1R)-1-[(difluoromethoxy)methyl]-2-[(4-fluorobenzyl)amino]-2-oxoethyl}carbamate,
(2R)-2-(Acetylamino)-N-benzyl-3-(difluoro-methoxy)propanamide,
tert-butyl {(1R)-1-[(difluoromethoxy)methyl]-2-[(3-fluoro-benzyl amino]-2-oxoethyl}carbamate,
tert-butyl {(1R)-1-[(difluoromethoxy)methyl]-2-[(3,4-difluorobenzyl)amino]-2-oxoethyl}carbamate,
Tert-butyl {(1R)-1-[(difluoromethoxy)methyl]-2-oxo-2-[(2-thienylmethyl)amino]ethyl}carbamate,
tert-butyl {(1R)-1-[(difluoromethoxy)methyl]-2-[(4-methyl-benzyl)amino]-2-oxoethyl}carbamate,
tert-butyl {(1R)-2-[(3-chlorobenzyl)amino]-1-[(difluoromethoxy)methyl]-2-oxoethyl}carbamate,
tert-butyl {(1R)-2-[(3-methyl benzyl)amino]-1-[(difluoromethoxy)methyl]-2-oxoethyl}carbamate,
tert-butyl {(1R)-1-[(difluoromethoxy)methyl]-2-oxo-2-[(3-thienylmethyl)amino]ethyl}carbamate,
(2R)-2-(Acetylamino)-3-(difluoromethoxy)-N-(4-fluorobenzyl)propanamide,
(2R)—N-benzyl-3-(difluoromethoxy)-2-[(methyl-sulfonyl)amino]propanamide,
(2R)-3-(difluoromethoxy)-N-(4-fluorobenzyl)-2-[(methylsulfonyl)amino]propanamide,
(2R)-2-(acetylamino)-N-(4-chlorobenzyl)-3-(difluoromethoxy)propanamide,
(2R)-2-(acetylamino)-3-(difluoromethoxy)-N-(3-fluorobenzyl)propanamide,
(2R)-2-(acetylamino)-N-(3,4-difluorobenzyl)-3-(difluoromethoxy)propanamide,
(2R)-2-(acetylamino)-3-(difluoromethoxy)-N-(2-thienylmethyl)propanamide, (2R)-2-(acetylamino)-3-(difluoromethoxy)-N-(4-methyl-benzyl)propanamide,
(2R)-2-(acetylamino)-N-(3-chlorobenzyl)-3-(difluoromethoxy)propanamide,
(2R)-2-(acetylamino)-3-(difluoromethoxy)-N-(3-methyl-benzyl)propanamide,
(2R)-2-(acetylamino)-3-(difluoromethoxy)-N-(3-thienyl-methyl)propanamide,
2-Acetylamino-N-benzyl-3-difluoromethoxy-propionamide,
2-Acetylamino-3-difluoromethoxy-N-(4-fluoro-benzyl)-propionamide, and
2-Acetylamino-N-(3,4-difluoro-benzyl)-3-difluoromethoxy-propionamide.

6. A compound selected from the group consisting of:
2-(Acetylamino)-N-benzyl-3-(difluoro-methoxy)propanamide;
2-(Acetylamino)-3-(difluoromethoxy)-N-(4-fluoro-benzyl)propanamide; and
(2R)-2-(acetylamino)-N-(4-chlorobenzyl)-3-(difluoromethoxy)propanamide.

7. A pharmaceutical composition comprising as active ingredient a therapeutically effective amount of a compound of claim 1 in association with one or more pharmaceutically acceptable diluents, excipients and/or inert carriers.

8. A method of treatment of epilepsy, neuropathic pain, acute and chronic inflammatory pain, migraine, or tardive dyskinesia, comprising the step of administering to a mammal in need thereof a therapeutically effective amount of a compound of claim 1.

9. A pharmaceutical composition comprising as active ingredient a therapeutically effective amount of a compound of claim 6 in association with one or more pharmaceutically acceptable diluents, excipients and/or inert carriers.

10. A method of treatment of epilepsy, neuropathic pain, acute and chronic inflammatory pain, migraine, or tardive dyskinesia, comprising the step of administering to a mammal in need thereof a therapeutically effective amount of a compound of claim 6.

* * * * *